US008610058B2

(12) United States Patent
Verbeck, IV et al.

(10) Patent No.: US 8,610,058 B2
(45) Date of Patent: Dec. 17, 2013

(54) SILVER AND SILVER NANOPARTICLE MALDI MATRIX UTILIZING ONLINE SOFT LANDING ION MOBILITY

(75) Inventors: Guido Fridolin Verbeck, IV, Plano, TX (US); Stephen Davila, Odessa, TX (US)

(73) Assignee: University of North Texas, Denton, TX (US)

( * ) Notice: Subject to any disclaimer, the term of this patent is extended or adjusted under 35 U.S.C. 154(b) by 208 days.

(21) Appl. No.: 13/287,499

(22) Filed: Nov. 2, 2011

(65) Prior Publication Data

US 2012/0104243 A1 May 3, 2012

Related U.S. Application Data

(60) Provisional application No. 61/409,851, filed on Nov. 3, 2010.

(51) Int. Cl.
*H01J 49/40* (2006.01)

(52) U.S. Cl.
USPC .......... 250/288; 250/281; 250/282; 250/286; 250/287

(58) Field of Classification Search
USPC .......................... 250/281, 282, 286, 287, 288
See application file for complete search history.

(56) References Cited

U.S. PATENT DOCUMENTS

| 7,122,792 B2 | 10/2006 | Chen et al. |
| 7,202,472 B2 | 4/2007 | Schmucker et al. |
| 2010/0090105 A1 | 4/2010 | Liang et al. |

OTHER PUBLICATIONS

Beavis, R.C., et al., Matrix-Assisted Laser-Desorption Mass Spectrometry Using 355mm Radiation, Rapid Commun. Mass Spectrom, (1989), 3 (12) 436-439.

Cohen, S.L, et al., "Influence of Matrix Solution Conditions on the MALDI-MS Analysis of Peptides and Proteins," Anal Chem., (1996), 68 (1) 31-37.

Dong, X., et al., "Graphene as a Novel Matrix for the Analysis of Small Molecules by MALDI-TOF MS," Anal. Chem., (2010), 82 (14) 6208-6214.

Go, E.P., et al., Desorption/Ionization on Silicon Time of Flight/Time of Flight, Mass Spectrometry, Anal. Chem., (2003), 75 (10), 2504-2506.

Guan, B., et al., "Characterization of Synthesized Titanium Oxide Nanoclusters by MALDI-TOF Mass Spectrometry," American Society for Mass Spectrometry, (2007) 18 (3) 517-524.

Knochenmuss, R., "Ion Formation Mechanisms in UV-MALDI," The Analyst, (2006), 131 (9) 966-986.

Pan, Chensong, et al., "Using Oxidized Carbon Nanotubes as Matrix for Analysis of Small Molecules by MALDI-TOF MS," American Society for Mass Spectrometry, (2005), 16 (6) 883-892.

(Continued)

*Primary Examiner* — Robert Kim
*Assistant Examiner* — Hanway Chang
(74) *Attorney, Agent, or Firm* — Edwin S. Flores; Chainey P. Singleton; Chalker Flores, LLP

(57) ABSTRACT

Silver nanoparticles as a sample matrix for Matrix Assisted Laser Desorption Ionization (MALDI) along with a novel method for nanoparticle development is described herein. The silver nanoparticles were generated from silver ions on the surface of a MALDI plate utilizing a Soft Landing Ion Mobility (SLIM) instrument. Upon interaction with the surface the incident silver ions were labile and aggregated into the nanoparticle structures in a time dependent fashion. Post landing analysis were completed by Time of Flight mass spectrometry (TOF), and of particular interest in the spectra were the elimination of low mass interference peaks that generally plague organic based matrices. The approach of the present invention significantly decreases sample preparation time and may lead to a preparation free MALDI source by soft landing a matrix directly on the sample surface.

39 Claims, 11 Drawing Sheets

(56) References Cited

OTHER PUBLICATIONS

Sherrod, S.D., et al., "Silver Nanoparticles as Selective Ionization Probes for Analysis of Olefins by Mass Spectrometry," Anal. Chem., (2008), 80 (17) 6796-6799.

Tanaka, K., et al., "Protein and Polymer Analyses up to <I>m/z<I> 100 000 by Laser Ionization Time-of-Flight Mass Spectrometry," Rapid Comm. Mass Spectrom, (1988), 2 (8), 151-153.

Wannier, G.H., Motion of Gaseous Ions in Strong Electric Fields, The Bell System Technical Journal, (1953), 32 (1) 170-254.

Wu, H.P., et al., "Gold Nanoparticles as Assisted Matrices for the Detection of Biomolecules in a High-Salt Solution through Laser Desorption/Ionization Mass Spectrometry," American Society for Mass Spectrometry, (2009) 20 (5) 875-882.

Xu, S., et al., "Carbon Nanotubes as Assisted Matrix for Laser Desorption/Ionization Time-of-Flight Mass Spectrometry," Anal. Chem. (2003), 75 (22) 6191-6195.

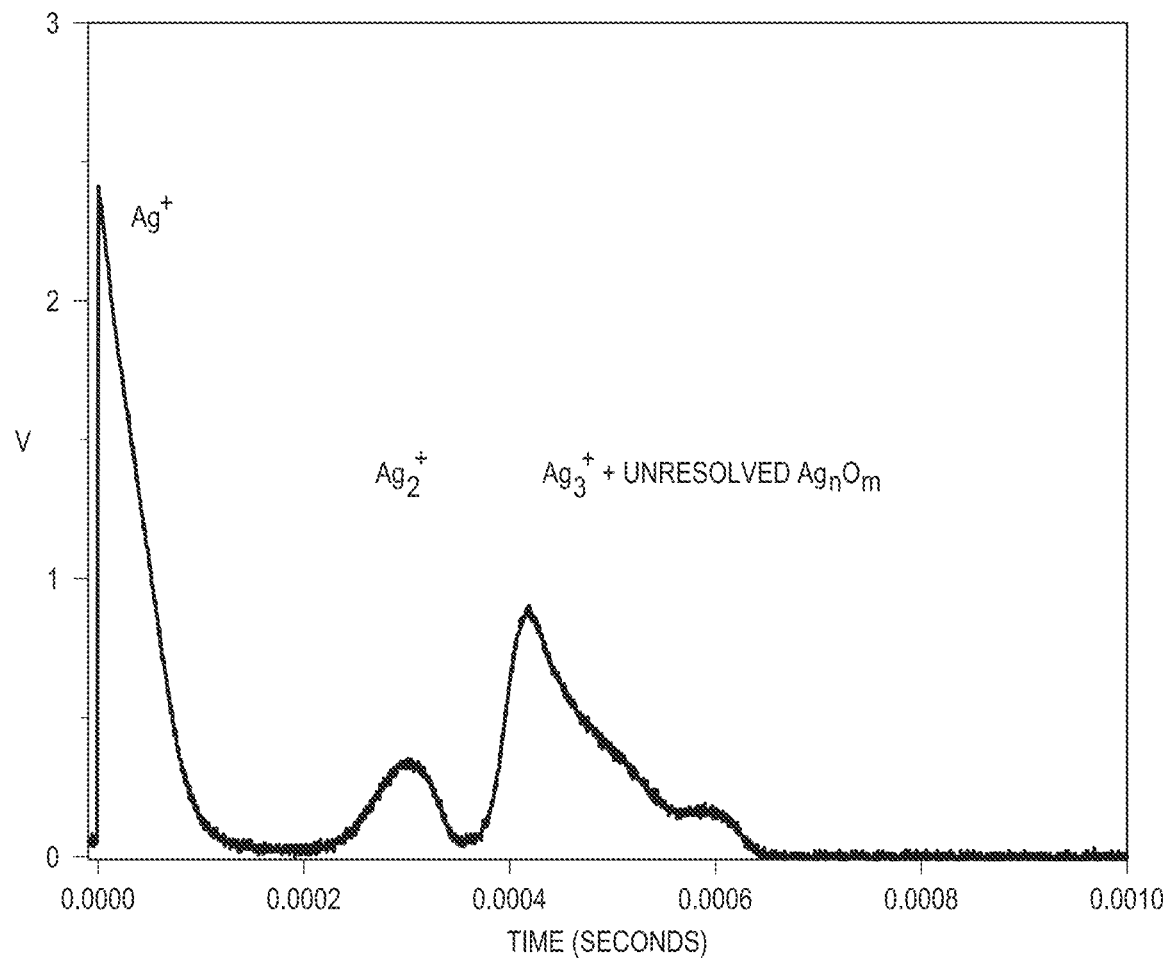

SILVER AND SILVER NANOPARTICLE MALDI MATRIX UTILIZING ONLINE SOFT LANDING ION MOBILITY

CROSS-REFERENCE TO RELATED APPLICATIONS

This application claims priority to U.S. Provisional Application Ser. No. 61/409,851, filed Nov. 3, 2010, the entire contents of which are incorporated herein by reference.

STATEMENT OF FEDERALLY FUNDED RESEARCH

This invention was made with U.S. Government support under Contract No. AFOSR-BAA-2007-7 awarded by the Air Force of Scientific Research (AFOSR). The government has certain rights in this invention.

TECHNICAL FIELD OF THE INVENTION

The present invention relates in general to the field of matrix assisted laser desorption ionization (MALDI) mass spectrometry, and more particularly to the use of silver nanoparticles as a sample matrix for MALDI analysis along with a novel method for nanoparticle development

INCORPORATION-BY-REFERENCE OF MATERIALS FILED ON COMPACT DISC

None.

REFERENCE TO A SEQUENCE LISTING

None.

BACKGROUND OF THE INVENTION

Without limiting the scope of the invention, its background is described in connection with MALDI matrices and sample preparation techniques.

U.S. Pat. No. 7,202,472 issued to Schmucker et al., 2007 relates to an improved method for mass spectrometric analysis, in particular for matrix-assisted laser desorption/ionization time-of-flight mass spectrometry (MALDI-TOF MS) using nanoparticles. In the Schmucker patent an analyte is added to a nanoparticle suspension, and the suspension containing the bound analyte is then deposited directly on a MALDI sample carrier and investigated by mass spectrometry, and to a nanoparticle suitable for this method.

U.S. Patent Application No. 2010/0090105 (Liang et al., 2010) discloses a plate for matrix-assisted laser desorption ionization (MALDI) mass spectrometry comprising an electrically conductive substrate (1) covered with a light sensitive matrix (2), the matrix (2) comprising a light absorber, a charge carrier, a probe molecule and a photo-sensitizer (3) arranged to oxidise the probe molecule when irradiated with light (4). The light sensitive matrix in the Liang invention comprises a xerogel containing semi-conducting nanoparticles and the photo-sensitizer comprises semi-conducting nanoparticles that absorb light at a wavelength substantially equal to that used for matrix-assisted laser desorption ionization. The semi-conducting nanoparticles of the Liang invention comprise titanium dioxide, zinc oxide or cadmium selenide.

U.S. Pat. No. 7,122,792 issued to Chen et al., (2006) provides a simple, rapid and cost-effective metal oxide-assisted laser desorption/ionization mass spectrometry (MOALDI MS) without the addition of light-absorbing organic-matrix, comprising the use of (a) an inorganic metal oxide with light absorbing capability as an assisting material to render desorption/ionization of samples in laser desorption/ionization mass spectrometry and (b) a citric acid buffer as the proton source for enhancing the ionization efficiency for analytes. Metal oxide assisting materials is not only restricted to the uses of films. Metal oxide nanoparticles are also suitable to be used as the assisting materials. Low matrix background, stable surface feature, homogeneous sample deposition, and wide detectable mass range are the merits of MOALDI MS.

SUMMARY OF THE INVENTION

The present invention relates to the use of silver nanoparticles as a sample matrix for Matrix Assisted Laser Desorption Ionization (MALDI) analysis of low mass analytes. In addition, the present invention also describes a novel method for nanoparticle development. The silver nanoparticles were generated from silver ions on the surface of a MALDI plate utilizing a Soft Landing Ion Mobility (SLIM) instrument. The novel silver nanoparticle matrix described herein eliminates or minimizes one or more low mass interference peaks from the MALDI-TOF spectra and increases a signal to noise (S/N) ratio in the MALDI-TOF spectra.

The present invention in one embodiment relates to a method for identifying, detecting, analyzing or combinations thereof of one or more low mass analytes by a matrix-assisted laser desorption/ionization-time of flight mass spectrometry (MALDI-TOF MS) technique comprising the steps of: (i) providing a liquid sample comprising the one or more low mass analytes to be identified, detected or analyzed, (ii) depositing the liquid sample on a surface of a MALDI plate or a substrate, wherein the liquid sample is dried on the surface of the MALDI plate or the substrate, (iii) depositing a matrix comprising one or more metal nanoparticles, clusters or combinations thereof on the surface of the MALDI plate or substrate comprising the dried liquid sample, wherein the metal nanoparticles or clusters are deposited or soft landed on the surface of the MALDI plate or substrate by a gas phase mobility soft landing method, wherein the soft landing method comprises a SLIM, a differential mobility analyzer, a drift tube or a flow tube comprising the steps of: a) providing an instrument comprising a drift region or a drift tube and a split-ring ion optic deflector, wherein the ion optic deflector helps selects and soft land a cluster of metal ions of a specific mobility, b) ionizing a target, a sample, a composition or a combinations thereof comprising at least one component capable of generating one or more metal ions by laser ablation in the instrument, c) separating and thermalizing the one or more metal ions in the drift region of the instrument by collision with a high pressure inert bath gas or gas mixture contained in the instrument, d) directing the thermalized metal ions using the split-ring ion optic from the drift tube to a landing surface, wherein the landing surface comprises the MALDI plate or the substrate, e) soft-landing the one or more metal ions on the MALDI plate or the substrate, and f) continuing the soft-landing for a specified period of time until a desired metal nanoparticle or cluster size is obtained, (iv) placing the MALDI plate or the substrate comprising the dried sample and the metal nanoparticle matrix in MALDI-TOF mass spectrometer, (v) obtaining a MALDI-TOF spectra by operating the MALDI-TOF mass spectrometer, and (vi) identifying, detecting or analyzing the one or more low mass analytes by a m/z ratio in the MALDI-TOF spectra.

In one aspect the low mass analytes comprise peptides, amino acids, small proteins, small molecules, organic compounds, organometallic compounds, inorganic compounds, and combinations or modifications thereof. In another aspect the one or more metal nanoparticles comprise silver, titanium, gold, platinum, palladium, nickel, cobalt, copper or manganese nanoparticles. In yet another aspect the nanoparticle is a silver nanoparticle. In a related aspect the one or more metal nanoparticles have an average size of about 10-500 nm. In another aspect the one or more metal nanoparticles have an average size of 10 nm, 25 nm, 50 nm, 75 nm, 100 nm, 150 nm, 200 nm, 225 nm, 250 nm, 275 nm, 300 nm, 350 nm, 400 nm, 450 nm, and 500 nm. In one aspect the metal nanoparticles eliminate or minimize one or more low mass interference peaks from the MALDI-TOF spectra. In another aspect the metal nanoparticles increase a signal to noise (S/N) ratio in the MALDI-TOF spectra. In yet another aspect the MALDI-TOF spectra may comprise one or more peaks relating to adduct products from the metal nanoparticles in the matrix.

Another embodiment of the present invention discloses a system for identifying, detecting or analyzing one or more low mass analytes in a sample comprising: a matrix-assisted laser desorption/ionization-time of flight mass spectrometry (MALDI-TOF MS) and a MALDI plate or a substrate comprising the sample and a matrix of one or more metal nanoparticles or clusters, wherein the MALDI plate or a substrate is placed in the MALDI-TOF MS, wherein the metal nanoparticles or clusters are deposited or soft landed on the MALDI plate or a substrate by a gas phase mobility soft landing instrument comprising: i) a soft landing chamber (SL) in a housing, ii) a laser source capable of generating a laser pulse or a radiation for an ionization of a target, a sample, a composition or a combination thereof comprising at least one component capable of generating one or more metal ions by laser ablation, iii) a drift region or a drift tube for separating and thermalizing the one or more metal ions by collisions with a high pressure inert bath gas or gas mixture contained in the drift tube, wherein an electric potential can be applied to the drift tube, wherein the drift tube further comprises two split rings placed at the two ends of the drift tube, for directing an ion cluster beam emanating from the drift tube, wherein a pulsed voltage can be applied to the split rings, iv) a high voltage power supply for powering the drift tube, generating an electric field for the migration of the one or more metal ions, v) a pulsing circuit for providing either a positive or a negative pulsed voltage, vi) a flange or similar arrangement to remove or replace the landing surface, wherein the landing surface comprises the MALDI plate or the substrate, and vii) a rotary vane rough pump for allowing the instrument to attain a low pressure.

In one aspect of the system described hereinabove the low mass analytes comprise peptides, amino acids, small proteins, small molecules, organic compounds, organometallic compounds, inorganic compounds, and combinations or modifications thereof. In another aspect the one or more metal nanoparticles comprise silver, titanium, gold, platinum, palladium, nickel, cobalt, copper or manganese nanoparticles. In a specific aspect the nanoparticle is a silver nanoparticle. In yet another aspect the one or more metal nanoparticles have an average size of about 10-500 nm. In another aspect the metal nanoparticles eliminate or minimize one or more low mass interference peaks from a MALDI-TOF spectra, increase a signal to noise (S/N) ratio in the MALDI-TOF spectra or both. In another aspect the MALDI-TOF spectra may comprise one or more peaks relating to adduct products from the metal nanoparticles in the matrix.

In yet another embodiment the present invention provides a method for depositing a matrix comprising one or more metal nanoparticles on a surface of a matrix-assisted laser desorption (MALDI) plate by a gas phase mobility soft landing method comprising the steps of: providing an instrument comprising a drift region or drift tube and a split-ring ion optic deflector, wherein the ion optic deflector helps selects and soft land a cluster of metal ions of a specific mobility, ionizing a target, a sample, a composition or a combinations thereof comprising at least one component capable of generating one or more metal ions by laser ablation in the instrument, separating and thermalizing the one or more metal ions in the drift tube of the instrument by collision with a high pressure inert bath gas or gas mixture contained in the drift tube, directing the thermalized metal ions using the split-ring ion optic from the drift tube to a landing surface, wherein the landing surface comprises the MALDI plate or the substrate, soft-landing the one or more metal ions on the MALDI plate or the substrate, and continuing the soft-landing for a specified period of time until a desired metal nanoparticle is obtained.

In one aspect the matrix is used to identify, detect or analyze one of more low mass analytes in a sample by a matrix-assisted laser desorption/ionization-rime of flight mass spectrometry (MALDI-TOF MS) technique, wherein the sample is deposited on the surface of the MALDI plate prior to depositing the one or more nanoparticles, wherein the low mass analytes comprise peptides, amino acids, small proteins, small molecules, organic compounds, organometallic compounds, inorganic compounds, and combinations or modifications thereof. In another aspect the one or more metal nanoparticles comprise silver, titanium, gold, platinum, palladium, nickel, cobalt, copper or manganese nanoparticles. In yet another aspect the nanoparticle is a silver nanoparticle. In another aspect the one or more metal nanoparticles have an average size of about 10-500 nm. In another aspect the one or more metal nanoparticles have an average size of 10 nm, 50 nm, 100 nm, 150 nm, 200 nm, 225 nm, 250 nm, 275 nm, 300 nm, 350 nm, 400 nm, 450 nm, and 500 nm.

In one embodiment the instant invention discloses an instrument for depositing a matrix comprising one or more metal nanoparticles on a surface of a matrix-assisted laser desorption (MALDI) plate by a gas phase mobility soft landing method comprising: a soft landing chamber (SL) in a housing, a laser source capable of generating a laser pulse or a radiation for an ionization of a target, a sample, a composition or a combination thereof comprising at least one component capable of generating the one or more metal ions to be deposited by laser ablation, a drift region or drift tube for separating and thermalizing the one or more metal ions by collisions with a high pressure inert bath gas or gas mixture contained in the drift tube, wherein an electric potential can be applied to the drift tube, wherein the drift tube further comprises two split rings placed at the two ends of the drift tube, for directing an ion cluster beam emanating from the drift tube, wherein a pulsed voltage can be applied to the split rings, a high voltage power supply for powering the drift tube, generating an electric field for the migration of the one or more metal ions, a pulsing circuit for providing either a lower positive or a lower negative pulsed voltage, a flange or similar arrangement to remove or replace the landing surface, wherein the landing surface comprises the MALDI plate, and a rotary vane rough pump for allowing the instrument to attain a low pressure. In one aspect the matrix is used to identify, detect or analyze one of more low mass analytes in a sample by a matrix-assisted laser desorption/ionization-time of flight mass spectrometry (MALDI-TOF MS) technique, wherein the sample is deposited on the surface of the MALDI plate prior to depositing the one or more nanoparticles, wherein the low mass analytes comprise peptides, amino acids, small proteins, small molecules, organic compounds organometallic compounds, inorganic compounds, and combinations or modifications thereof. In another aspect the one or more metal nanoparticles comprise silver, titanium, gold, platinum, palladium, nickel, cobalt, copper or manganese nanoparticles. In yet another aspect the nanoparticle is a silver nanoparticle. In one aspect the one or more metal nanoparticles have an average size of about 10-500 nm.

Another embodiment of the instant invention relates to a method for identifying, detecting, analyzing or combinations thereof of one or more peptides by a matrix-assisted laser desorption/ionization-time of flight mass spectrometry (MALDI-TOF MS) technique comprising the steps of: (i) providing a liquid sample comprising the one or more peptides to be identified, detected or analyzed, (ii) depositing the liquid sample on a surface of a MALDI plate, wherein the liquid sample is dried on the surface of the MALDI plate, (iii) depositing a matrix comprising one or more silver nanoparticles on the surface of the MALDI plate comprising the dried liquid sample, wherein the silver nanoparticles are soft landed on the surface of the MALDI plate by a gas phase mobility soft landing method comprising the steps of: providing an instrument comprising a drift region or drift tube and a split-ring ion optic deflector, wherein the ion optic deflector helps selects and soft land a cluster of silver ions of a specific mobility, ionizing a silver rod capable of generating one or more silver ions by laser ablation in the instrument, separating and thermalizing the one or more silver ions in the drift tube of the instrument by collision with helium gas or gas mixture contained in the drift tube, directing the thermalized metal ions using the split-ring ion optic from the drift tube to the MALDI plate, soft-landing the one or more silver ions on the MALDI plate, and continuing the soft-landing for a specified period of time until a desired silver nanoparticle size is obtained, (iv) placing the MALDI plate comprising the dried sample and the silver nanoparticle matrix in MALDI-TOF mass spectrometer, (v) obtaining a MALDI-TOF spectra by operating the MALDI-TOF mass spectrometer, and (vi) identifying, detecting or analyzing the one or more peptides by a m/z ratio in the MALDI-TOF spectra.

In one aspect the peptides comprise tyrosine-histidine (YH) or tyrosine-histidine-tryptophan (YHW). In another aspect the one or more silver nanoparticles have an average size of about 10-500 nm. In yet another aspect the one or more silver nanoparticles have an average size of 10 nm, 25 nm, 50 nm, 75 nm, 100 nm, 150 nm, 200 nm, 225 nm, 250 nm, 275 nm, 300 nm, 350 nm, 400 nm, 450 nm, and 500 nm. In one aspect the silver nanoparticles eliminate or minimize one or more low mass interference peaks from the MALDI-TOF spectra. In one aspect the silver nanoparticles increase a signal to noise (S/N) ratio in the MALDI-TOF spectra. In another aspect of the instant invention the MALDI-TOF spectra may comprise one or more peaks relating to adduct products from the silver nanoparticles in the matrix.

In yet another embodiment the instant invention discloses a system for identifying, detecting or analyzing one or more peptides in a sample comprising: a matrix-assisted laser desorption/ionization-time of flight mass spectrometer (MALDI-TOF MS) and a MALDI plate comprising the sample and a matrix of one or more silver nanoparticles, wherein the MALDI plate or a substrate is placed in the MALDI-TOF MS, wherein the silver nanoparticles are deposited or soft landed on the MALDI plate by a gas phase mobility soft landing instrument comprising: (i) a soft landing chamber (SL) in a housing, (ii) a laser source capable of generating a laser pulse or a radiation for an ionization of a silver rod for generating one or silver metal ions by laser ablation, (iii) a drift region or drift tube for separating and thermalizing the one or more silver ions by collisions with a high pressure helium gas or gas mixture contained in the drift tube, wherein an electric potential can be applied to the drift tube, wherein the drift tube further comprises two split rings placed at the two ends of the drift tube, for directing an ion cluster beam emanating from the drift tube, wherein a pulsed voltage can be applied to the split rings, (iv) a high voltage power supply for powering the drift tube, generating an electric field for the migration of the one or more silver ions, (v) a pulsing circuit for providing either a positive or a negative pulsed voltage, (vi) a flange or similar arrangement to remove or replace the MALDI plate, and (vii) a rotary vane rough pump for allowing the instrument to attain a low pressure. In one aspect the one or more silver nanoparticles have an average size of about 10-500 nm. In another aspect the silver nanoparticles eliminate or minimize one or more low mass interference peaks from the MALDI-TOF spectra. In yet another aspect the silver nanoparticles increase a signal to noise (S/N) ratio in the MALDI-TOF spectra. In one aspect the MALDI-TOF spectra may comprise one or more peaks relating to adduct products, clusters or both relating to the silver nanoparticles in the matrix.

BRIEF DESCRIPTION OF THE DRAWINGS

For a more complete understanding of the features and advantages of the present invention, reference is now made to the detailed description of the invention along with the accompanying figures and in which:

FIG. 5 shows the ion mobility spectrum of the laser ablated silver rod exhibiting multiple peaks corresponding to Ag$^+$, Ag$^{2+}$, and Ag$^{3+}$ peaks;

DETAILED DESCRIPTION OF THE INVENTION

Figure 1:
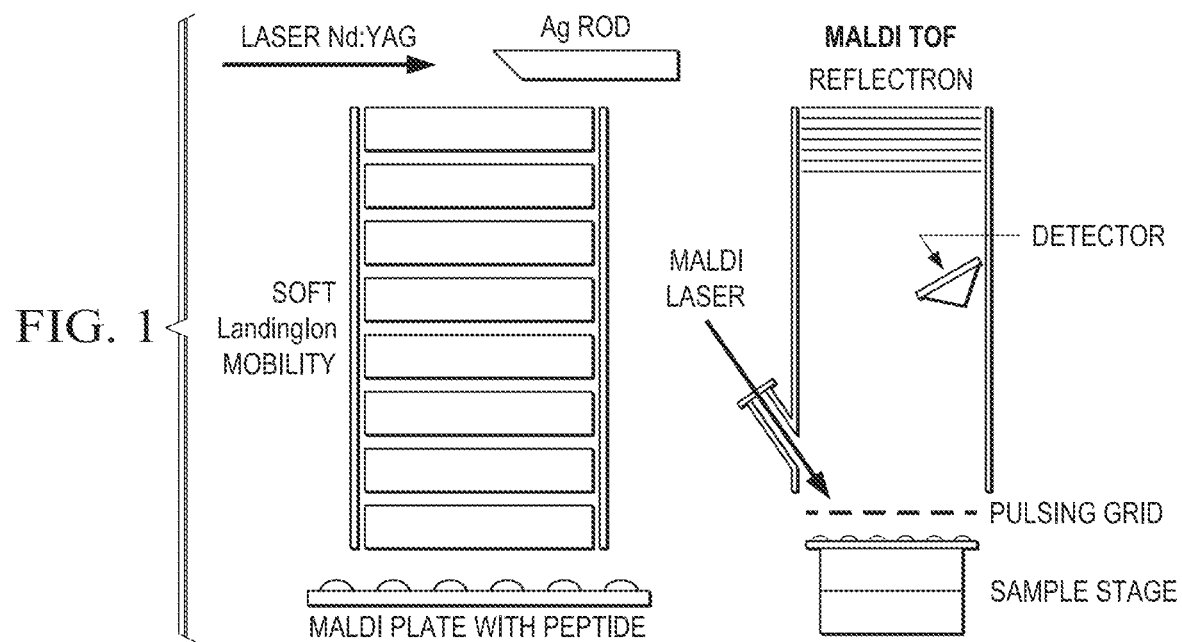
FIG. 1 is a schematic representation of SLIM-MALDI process: Left: shows soft-landing of nanoparticles on a surface spotted with analyte, Right: analysis of surface using MALDI.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry," U.S. Pat. No. 6,124,137, entitled "Surface-Enhanced Photolabile Attachment And Release For Desorption And Detection Of Analytes;" Wright et al., Prostate Cancer and Prostatic Diseases 1999, 2: 264-76; and Merchant and Weinberger, Electrophoresis 2000, 21: 1164-67.

The term "laser ablation" refers to the evaporation or removal of the target material by the focused energy of the laser beam. The bulk target material is converted into vapor components of atoms, ions, clusters, and particles. These vapor components are collected on the heated substrate and form a thin film.

According to the present invention, the term "nanoparticles" refers to the size distribution of the particles constituting the corresponding material that includes particles of nanometer scale in size. Typically "nanoparticles" have an average diameter of 1 μm or less, preferably from 10 to 500 nm, and more preferably from 10 to 100 nm. In addition, it is preferred that the particle size distribution of the metal nanoparticles is such that 50% or more, preferably 70% or more, more preferably 90% or more of the particles having a diameter of 1 μm or less.

Matrix Assisted Laser Desorption Ionization (MALDI) has become a powerful tool, but has been burdened with labor intensive sample preparation. The present invention describes the utility of silver nanoparticles as a sample matrix along with a novel method for nanoparticle development. Silver nanoparticles were generated from silver ions on the surface of a MALDI plate utilizing a Soft Landing Ion Mobility (SLIM) instrument developed by the present inventors. Upon interaction with the surface the incident silver ions were labile and aggregated into the nanoparticle structures in a time dependent fashion. A deposition of 10 minutes lead to an average nanoparticle diameter of 200 nm contrasted with an average diameter of 500 nm at 60 minutes of deposition. Post landing analyses were completed by Time of Flight mass spectrometry (TOF), and of particular interest in the spectra were the elimination of low mass interference peaks that generally plague organic based matrices. Based on these eliminations, low mass analytes were chosen which included a single amino acid, a dipeptide, and a tripeptide manifested in Y, YH, and YHW respectively. The lack of low mass interferences allowed all analytes to be seen along with the silver adduct peak in some cases. Also noted in these spectra were the lack of fragmentation and an increased signal to noise ratio, indicating that silver being deposited was acting as a suitable matrix. This SLIM-MALDI based approach significantly decreases sample preparation time and may lead to a preparation free MALDI source by soft landing a matrix directly on the sample surface. FIG. 1 is a schematic representation of SLIM-MALDI process. The diagram on the left shows the soft-landing of nanoparticles on a surface spotted with analyte and the diagram on the right shows the analysis of the surface using MALDI.

Since the inception of MALDI a great number of molecules have been characterized with speed and efficiency [1-6]. MALDI has become an important technique in the analysis of biomolecules, but it is not without disadvantages. The exact mechanism of ionization is not known, however one of the leading mechanisms states that there is an energy transfer to the analyte from the UV absorbing matrix [7]. The matrix absorbs most of the radiation allowing the protein to stay cool and intact when the laser strikes the sample surface, initiating desorption and ionization [8]. Organic matrices are susceptible to ionization and therefore produce high background noise in the low mass region. This places a fundamental restriction on the applicability of MALDI to analyses in the high molecular weight region. Sample preparation, which involves mixing of analyte and matrix, has also posed a problem for MALDI because of inhomogeneity of the matrix/analyte crystals [9]. Inhomogeneity gives rise to inconsistent analyte signal across the sample surface. These problems have led to much research in alternative matrices, and nanoparticles have gained a lot of attention in the recent past [10-16]. Nanoparticles have been shown to serve as reservoirs of photon energy as Tanaka demonstrated with the use of 30 nm cobalt nanoparticles for the laser desorption/ionization of proteins in the presence of glycerol [14]. At particle sizes>500 μm nanoparticles appear to be independent of the irradiating wavelength and can act as a matrix from UV- to near IR wavelengths. Nanoparticles also have the tendency to be more flexible in terms of sample preparation (pH, solvents, salts, etc.) [10]. Additionally, the application of graphite, silicon films, silicon nitrate, self-assembled germanium nanodots, and titanium oxide have been found to significantly reduce background noise in the low mass region when compared to standard organic matrices [12, 17-21].

Nanoparticles of silver and gold have been found to be suitable matrices for MALDI, Laser Desorption Ionization (LDI) and Surface Assisted Laser Desorption Ionization (SALDI) [10, 16, 22-25]. As matrices, these nanoparticles produce a cleaner spectrum, have high photoabsorptivity and large surface areas, thus making them uniquely suited for matrices in MALDI [16].

The studies of the present invention relates to the use of Soft Landing Ion Mobility (SLIM) to soft land silver clusters onto a sample plate containing low molecular weight peptides, creating a SLIM-MALDI source. Post landing analyses are completed using MALDI TOF-MS with the goal of developing a quick, low preparation SLIM-MALDI source. Deposition of silver nanoparticles is accomplished using SLIM and is described in greater detail elsewhere [26]. Soft landing is a technique whereby ionized molecules or clusters are deposited intact onto a surface. This technique is used in the isolation, purification and characterization of new materials formed through this preparative technique [27-31]. SLIM utilizes the drift tube to thermalize the ions to kinetic energy (KE) values that are <1 eV. Sub-eV deposition enables SLIM to deposit ions onto a hard substrate with little to no translational motion across the surface. The instrument described herein has a unique ion optic deflector which enables the user to select and soft land a cluster of a specific mobility, reducing the amount of time and tedious preparation of nanoparticles. The theory behind ion mobility is described in greater detail elsewhere, but the kinetic energy (KE) of the ion is calculated using Equation 1 where ion mass (m), mass of buffer gas (M), charge of ion (z), elementary charge (e), Boltzmann's constant ($k_b$), buffer gas temperature (T), number density of the gas (N), and field strength ($E_0$) [32-37]. The KE of the ion exiting the drift tube can be calculated by substituting K for velocity in the classical KE equation. The energy of the ion can be obtained by solving Equation 1 [26].

$$K_E = \frac{18\pi z^2 e^2 R^2}{513 k_b N_A} \frac{E^2 T}{P^2 \Omega^2}\left(1 + \frac{m}{M}\right) \quad (1)$$

By incorporating core foundation principles of Ion Mobility to SLIM coupled with laser ablation it is possible to produce and deposit nanoparticles in order to make a low preparation SLIM-MALDI nanoparticle source capable of producing a variety of nanoparticles for use as MALDI matrices.

Figure 2:
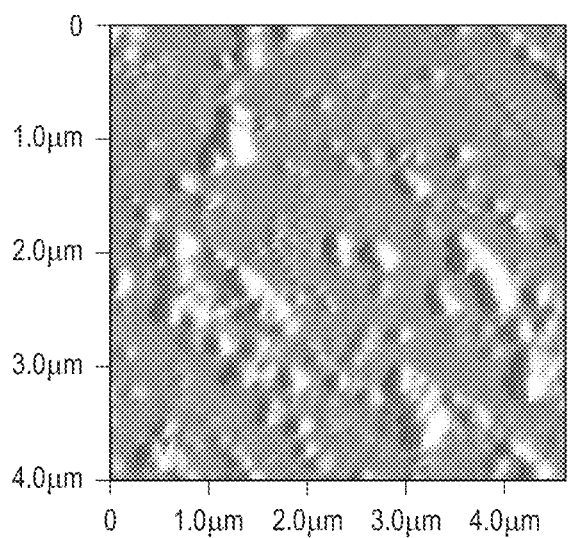
FIG. 2 is an atomic force microscopy (AFM) image showing the aggregation of Cu into micro size particles on mica.

Aggregation of nanoparticles: The mechanism and aggregation of soft landed ionized clusters on a surface is not completely understood, but in the present invention deposition and aggregation occurs at sites around the surface where the $Ag_n^+$ clusters can become neutral. This neutralization site would then allow subsequent $Ag_n^+$ clusters to aggregate at that particular location in order for neutralization to occur, meanwhile allowing the site to grow to nanoparticle size. Previous work and characterization of soft landed $CuO^+$ on muscovite (mica, $KAl_2Si_3AlO_{10}(OH)_2$) (SPI Supplies, West Chester, Pa.) were carried out using SLIM and Atomic Force Microscopy (AFM). AFM Images of the mica surface for CuO exhibited striation patterns along the surface and bridging over defects in the surface, showing self-assembly had occurred since the defects were left unfilled[26]. The mechanism for deposition were perplexing since mica is an insulator and should not have been able to neutralize the charge of the $CuO^+$, however there is a preferential site for charge transfer to occur. Defect sites within the lattice of the muscovite (along the 001 plane) where a K atom is simply not present or was removed along with upper layer during the mechanical exfoliation process allow for charge transfer [38]. This defect site allows the ion to become neutral and become a site for future nanoparticle growth. AFM images of Cu on mica exhibiting this type of aggregation into micro size particles as shown in FIG. 2.

Figure 3:
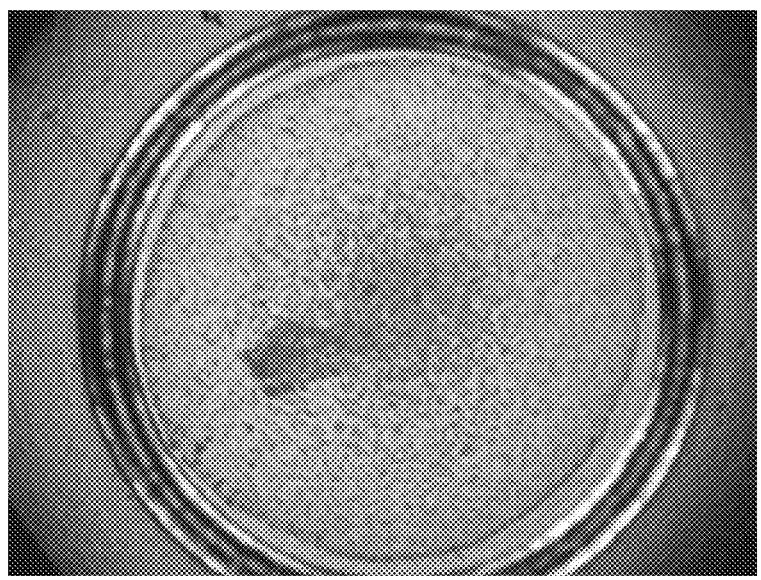
FIG. 3 is an image of a MALDI plate after deposition of the Ag nanoparticles. The Ag nanoparticles can visibly be seen in the dried peptide.
Figure 4A:
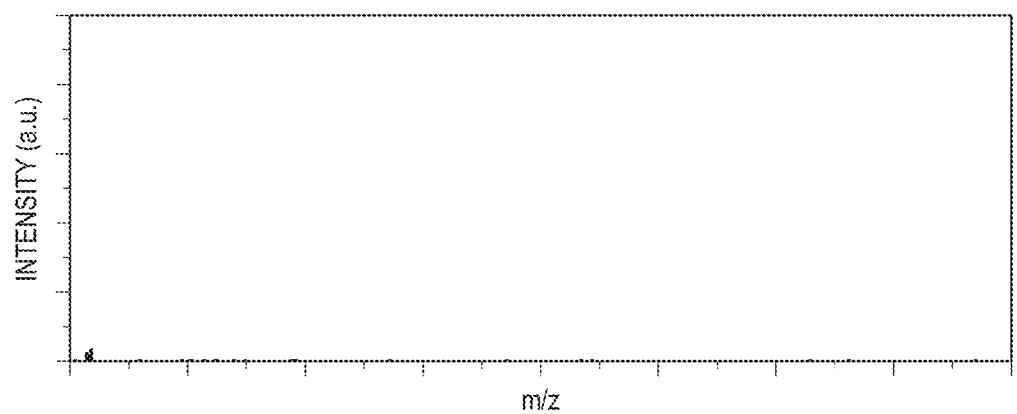
FIGS. 4A and 4B show a MALDI analysis was performed on a MALDI plate not landed with Ag nanoparticles spotted with peptide solutions of Y (FIG. 4A) and YH (FIG. 4B) (1:1, V:V MeOH/H$_2$O with/0.1% TFA)
Figure 4B:
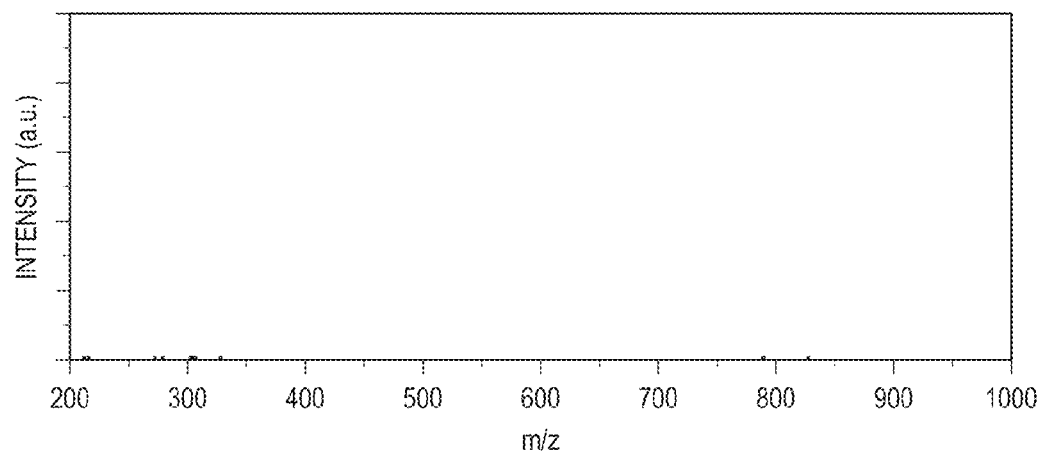
Figure 6A:
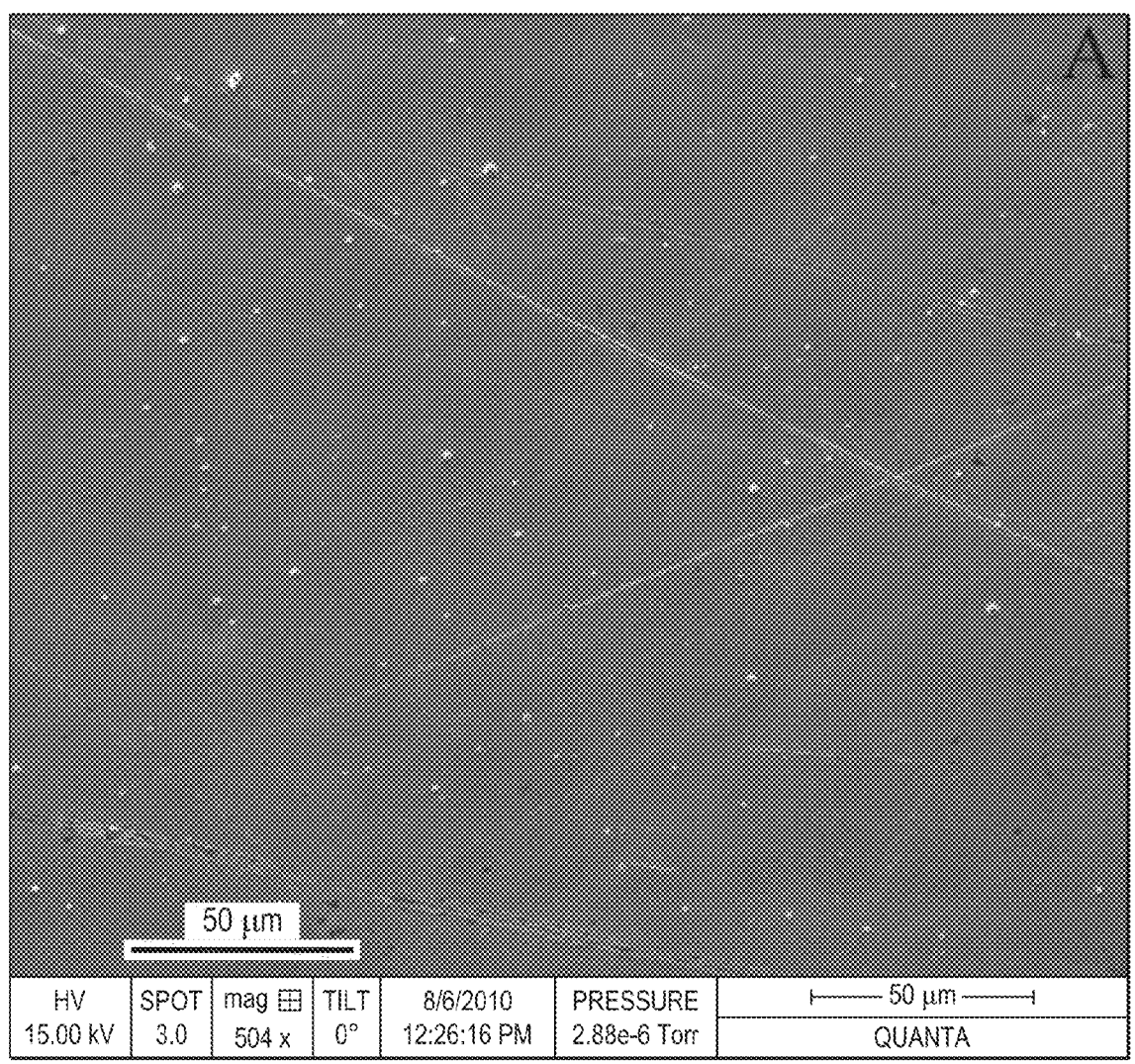
FIGS. 6A and 6B show the surface of the MALDI plate spotted with peptide for 30 (FIG. 6A) and 60 minutes (FIG. 6B)
Figure 6B:
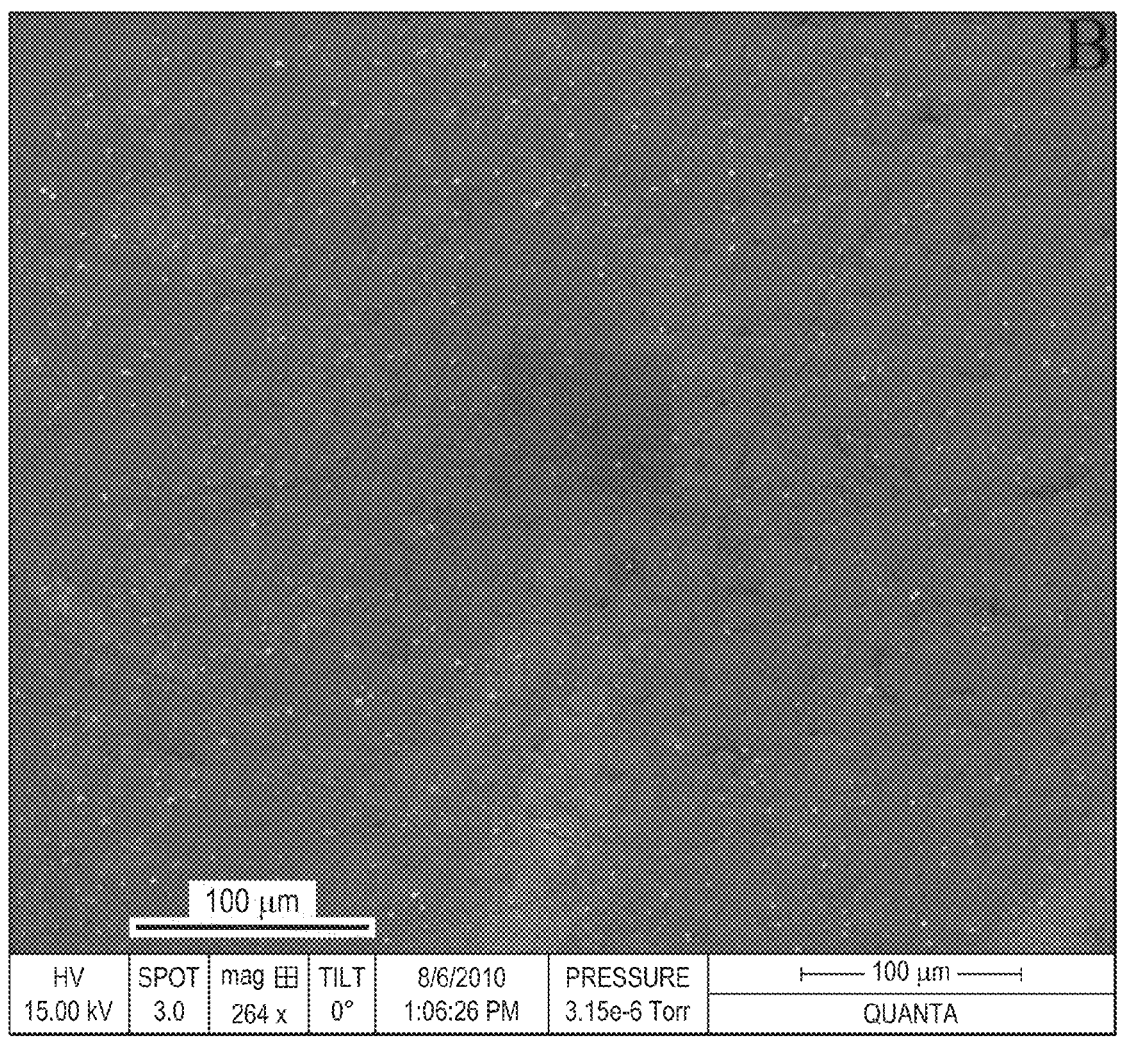

FIG. 3 shows an image of a MALDI plate after deposition of the Ag nanoparticles. The Ag nanoparticles can visibly be seen in the dried peptide. FIGS. 4A and 4B show a MALDI analysis was performed on a MALDI plate not landed with Ag nanoparticles spotted with peptide solutions of Y and YH (1:1, V:V MeOH/$H_2O$ with/0.1% TFA), respectively.

Peptide coated beads are prepared using a simple, rapid, and solvent-free technique which incorporates ammonia ($NH_3$) gas at high-pressure in a Parr reactor to cleave the peptide from a solid support based of 4-hydroxymethyl benzoic acid (HMBA) linker (peptide synthesis and chain protection is described in greater detail elsewhere)[39]. Tyrosine (Y), Tryptophan (W), and Histidine (H), were used in the synthesis of the following peptides YH and YHW. A bulk extraction of coated beads is carried out by placing 1 mg of the desired peptide coated bead into 1 mL of a 1:1(V:V) MeOH/$H_2O$ with 0.1% TFA solution. The solution is vortexed for 30 seconds to affect dissolution and then centrifuged for 10 minutes. A gold coated MALDI plate is spotted with 1 µL droplets of peptide solution and allowed to dry (10 minutes). After the peptide droplets have dried the plate is placed into the SLIM chamber which was then rough vacuumed until the pressure is below 20 mTorr. The chamber is then back filled with He gas and voltages set to values that corresponds to the desired deposition kinetic energy (KE). Silver clusters are formed via laser ablation of 3N silver rod (99.999% purity, SPI Supplies, West Chester, Pa.), with a 532 nm Nd:YAG (Minilite, Continuum, Santa Clara, Calif.) in the presence of a He drift gas. The drift tube is operated with a field (E) of 30 V/cm and at a pressure of 2 Torr. This low pressure/high field configuration enables the silver clusters to have a higher KE than at low pressure and low field. The cause for aggregation is under investigation but the silver ions may have a preferential bonding site to the peptide, causing subsequent ions to be directed to the initial landing site, enabling the silver cluster ions to aggregate in a manner similar to that of the muscovite landing described above. The other possibility for aggregation is based on the KE of the ion. A higher KE would allow the ions to have a greater range of translational motion on the surface when they are deposited, causing the clusters to aggregate into nanoparticle size structures. A series of studies to find optimum nanoparticle size on the surface were conducted with preparation procedures the same as above, except that deposition time varied at 5, 10, 30, and 60 minute intervals for each of the plates. The results of the study are presented below with a nominal deposition time of 10-15 minutes.

FIG. 3 shows the MALDI plate after deposition of the Ag nanoparticles where one can visibly see the silver particles in the dried peptide. After deposition of the silver nanoparticles the prepared peptides are loaded into the MALDI-TOF (Vestec RBT2, Vestec, Houston, Tex.). Positive ion MALDI-TOF spectra are acquired using a 20 kV pulse, with a 100 laser shot acquisition using a UV nitrogen laser (VSL-337ND, LSI, Franklin, Mass.). In order to compare the soft landed Ag nanoparticle matrix with a standard MALDI matrix, the amino acid and 2 peptide solutions were mixed in a 1:20 ratio with a 1 mL solution of α-cyano-4-hydroxycinnamic acid (CHCA) 10 mg/mL solution (CHCA in 1:1, V:V ACN/H$_2$O with/0.1% TFA) and run using the same MALDI-TOF parameters described above. A third comparison shown in FIGS. 4A and 4B was performed between the Ag nanoparticle matrix and that of MALDI plate spotted with peptide solutions of Y and YH (1:1, V:V MeOH/H$_2$O with/0.1% TFA) under the same conditions but were not landed with Ag nanoparticles. All spectra were gathered under the same conditions in order to compare the Ag nanoparticle matrix contribution vs. no matrix runs to ensure the TOF spectra collected in FIGS. 8A, 8B, 9A, 9B, and 10B are not combinations of Ag nanoparticles with desorbed peptides from the sample surface.

The ion mobility spectrum of the laser ablated silver rod (FIG. 5) exhibits multiple peaks. The predominant peaks in the Ion Mobility spectrum correspond to Ag$^+$, Ag$_2^+$, and Ag$_3^+$ peaks. The initial peak in the spectrum is that of Ag$^+$, and the reduced mobility was calculated using mobility equations based on the drift time [40]. A reduced mobility value of 19±1 cm$^2$/Vs was calculated and compared to the reduced mobility of Ag$^+$ reported previously in the literature and found that our initial peak assignment is in agreement with the literature [40-42]. The remaining peaks in the spectra belong to Ag$_2^+$ and Ag$_3^+$ along with the corresponding Ag$_n$O$_m^+$ clusters. Even though the peaks of Ag$_2^+$ and Ag$_3^+$ are not well resolved, we are still able to deposit Ag$_n^+$ (n=2-3) clusters on to the dried protein surface creating a nanoparticle matrix using Ag clusters.

Figure 7A:
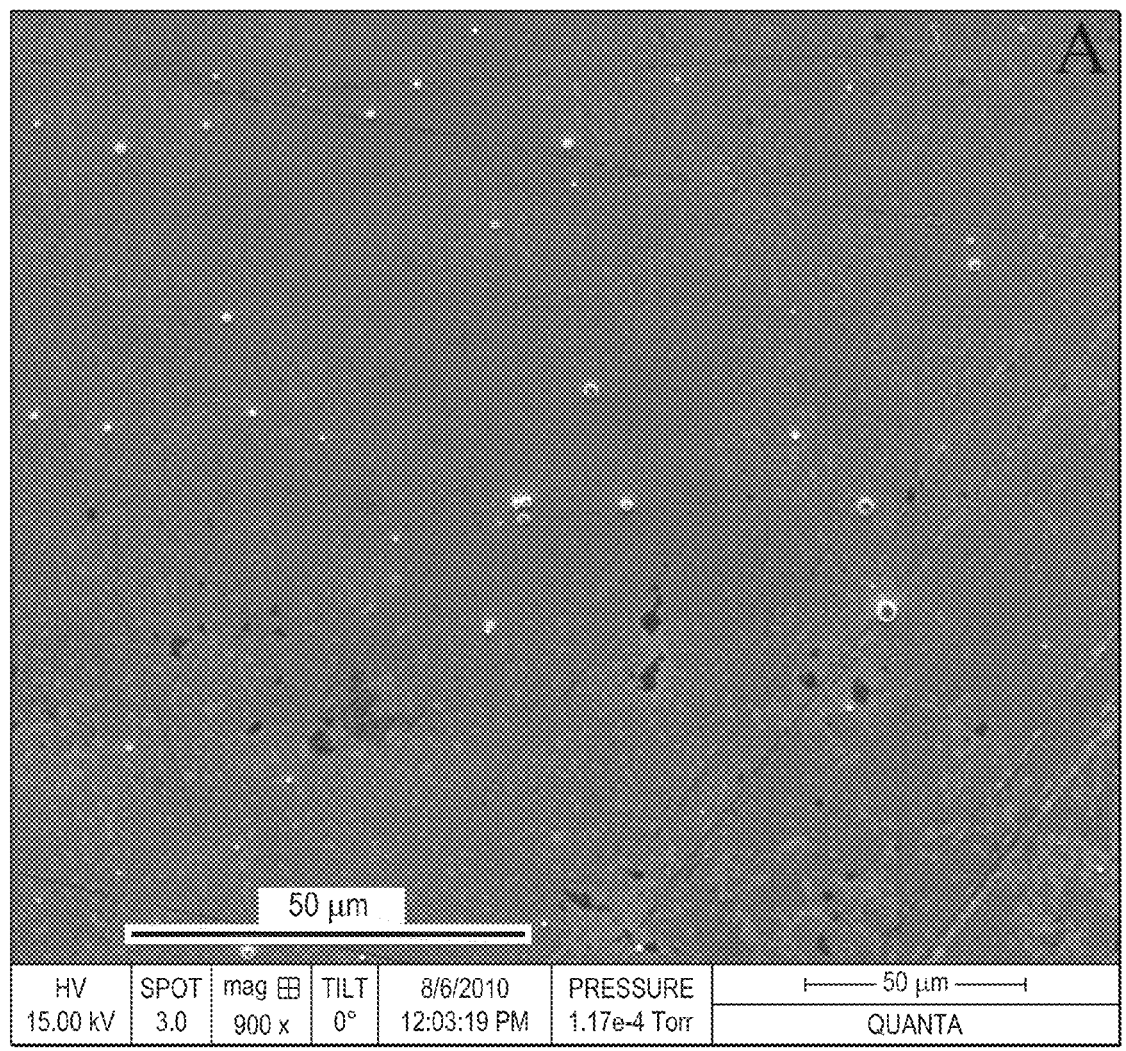
FIGS. 7A and 7B show images of Ag nanoparticles on the surface (FIG. 7A) and close up of the Ag nanoparticle (FIG. 7B)
Figure 7B:
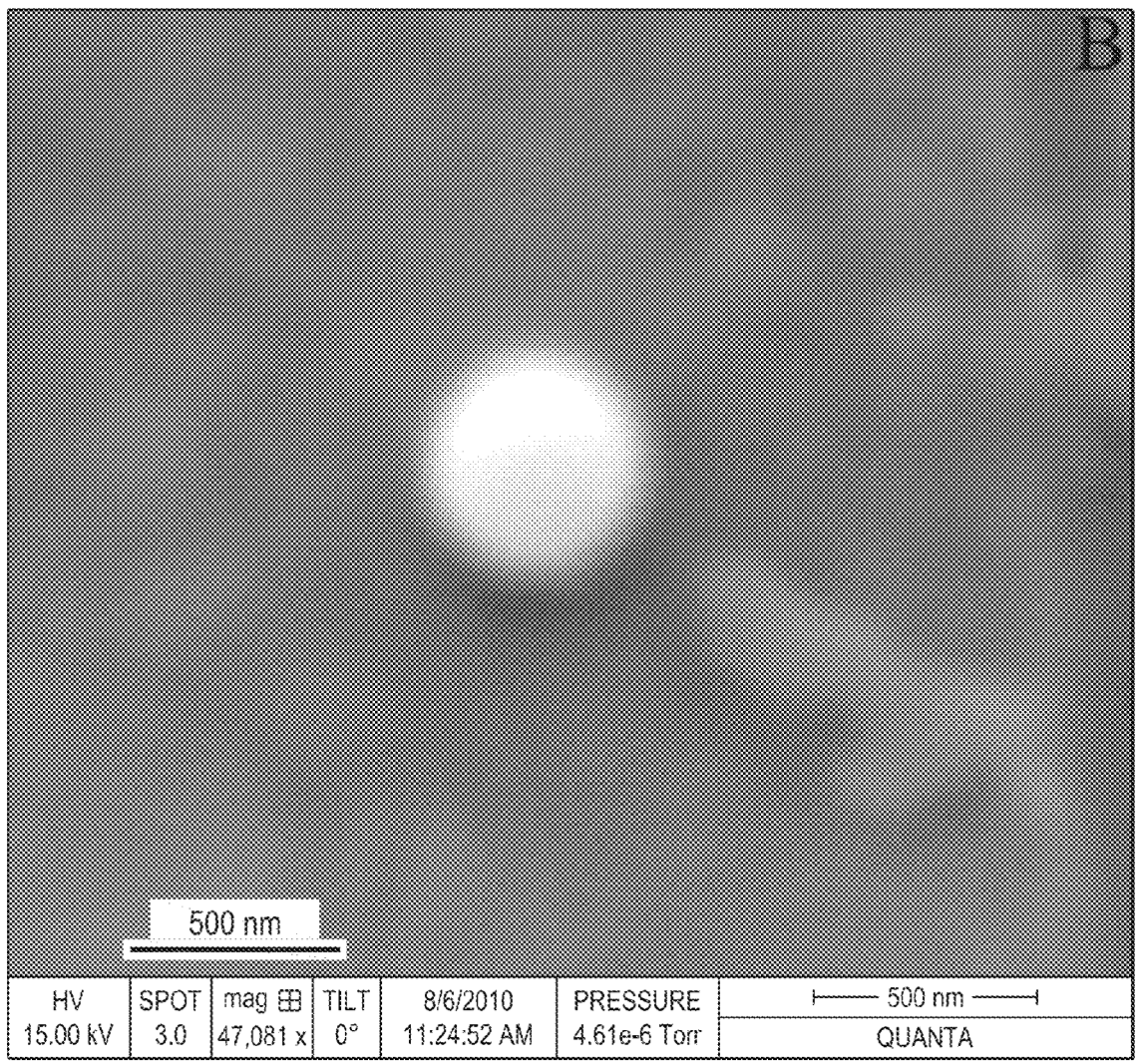

SEM images of the nanoparticles were taken of the surface at four time intervals 5, 10, 30, and 60 minutes. Images shown in FIGS. 6A, 6B, 7A and 7B are of the surface of the MALDI plate spotted with peptide for 30 and 60 minutes (FIGS. 6A and 6B) and a close up of the Ag nanoparticle (FIG. 7B). Counting the nanoparticles present in the image an average nanoparticle distribution of 33-39 nanoparticles per 100 μm×100 μm area at 5 minutes, with an average nanoparticle size between 200-300 nm. As the deposition time increases the number of nanoparticles per area also increases as does the average size of the particles. At 30 min the average particle size range has increased from 200-500 nm, with larger size particles occurring more frequently and coverage increasing to 52-60 particles per 100 μm×100 μm area. By controlling the KE of the ions through adjustments to the field, pressure or laser intensity we can affect the size and distribution of the Ag nanoparticles on the surface.

The MALDI-TOF spectra of the soft landed Ag nanoparticle matrix are shown in FIGS. 8A, 8B, 9A, 9B, and 10B for Y (m/z=180), YH (m/z=318), and YHW (m/z=503). The first two sets of peaks in FIGS. 8B, 9B, and 10B belong to that of Ag$_2^+$, Ag$_3^+$, and their respective isotopes. Upon further expansion of the silver cluster portion of the spectrum we can view the isotope ratio of the Ag$_n^+$ clusters with 3 peaks at m/z 214, 216, 218 belonging to the n=2 cluster of Ag$_n^+$, along with m/z 321, 323, 325, 327 forming the isotope combinations for Ag$_3^+$. These cluster peaks may also act as markers for calibration in the low mass range. The peaks marked in figures FIGS. 8A, 8B, 9A, 9B, and 10B correspond to that of the peptide that has either undergone protonation [Y+H]$^+$ (m/z=181), experienced loss of H$_2$O [YH—H$_2$O]+H$^+$ (m/z=301) or an adduct to a silver atom [YHW+Ag]$^+$ (m/z=610, 612). The exact mechanism or cause of Ag adducting is still under investigation. A few possibilities for this interaction may be based on the amount of analyte placed on the surface. Small amounts of analyte (<2 μL droplets) dried onto the surface may have strong interactions with the Ag nanoparticles through their π systems. Another possibility may be based on the KE of the Ag clusters. A KE>1 eV may allow the Ag$_n^+$ cluster to become implanted or allow it to diffuse into the substrate and bind to the peptide [43, 44]. The TOF spectra of these soft landed nanoparticle matrices show no low mass interference, as is the usual case when standard matrices (CHCA) are used. FIGS. 8C, 8D, 9C, 9D, and 10A show the MALDI-TOF spectra of the analytes prepared with CHCA. TOF spectra of the peptides used with CHCA exhibits multiple peaks and significant matrix/analyte interference in the low mass ranges (between m/z 150-250), as one of the amino acids (Y+H) is buried within the matrix at m/z 181.

Figure 8A:
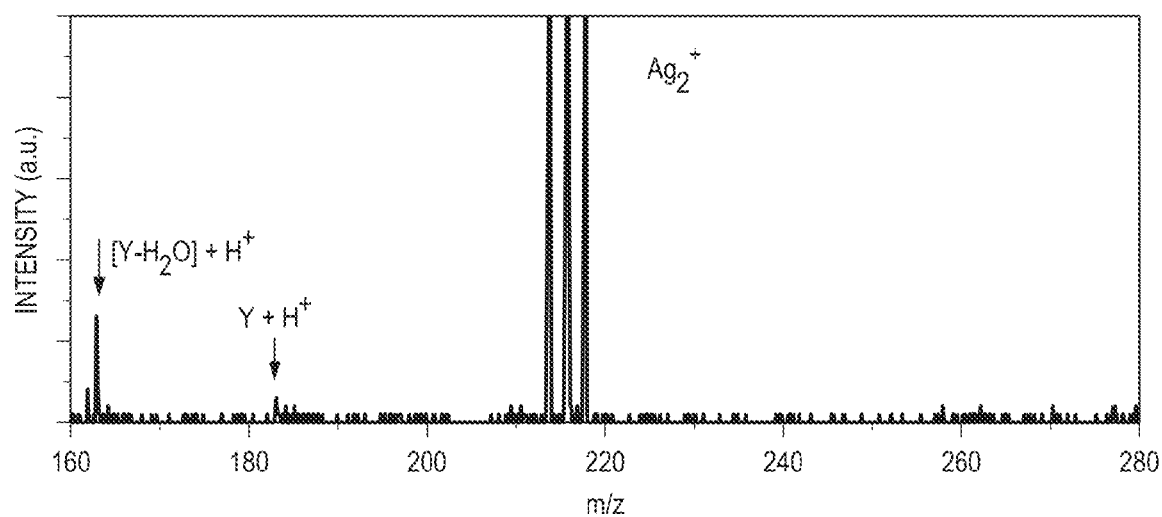
FIGS. 8A-8D show: the magnified MALDI-TOF spectra of Y peptide with Ag nanoparticles (FIG. 8A), original MALDI-TOF spectra of Y with Ag nanoparticles showing no low mass interference with peptide (FIG. 8B), magnified MALDI-TOF spectra of Y in CHCA matrix (FIG. 8C), and original MALDI-TOF spectra of Y in CHCA matrix showing low mass interference with peptide (FIG. 8D)
Figure 8B:
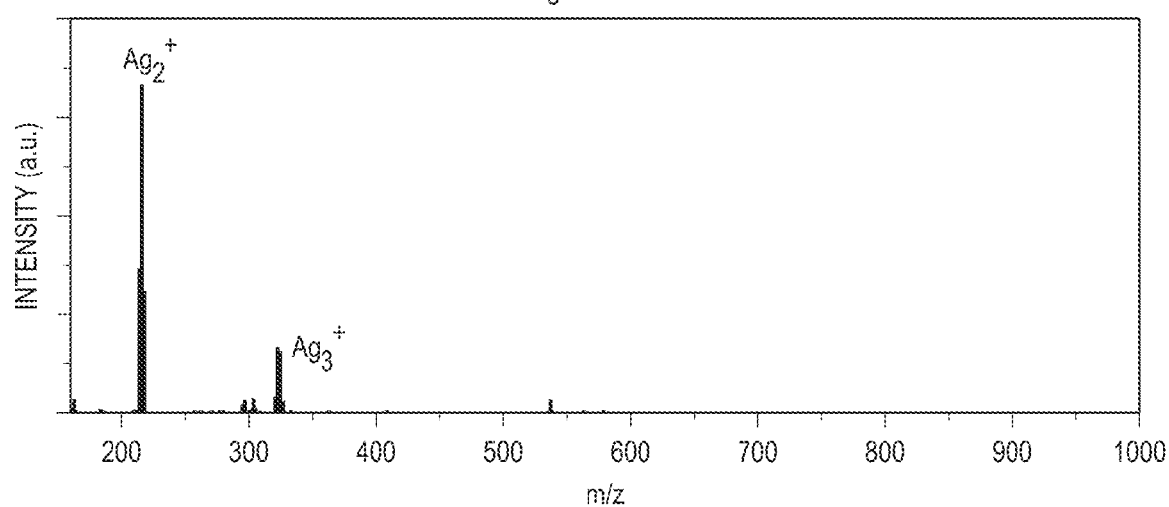
Figure 8C:
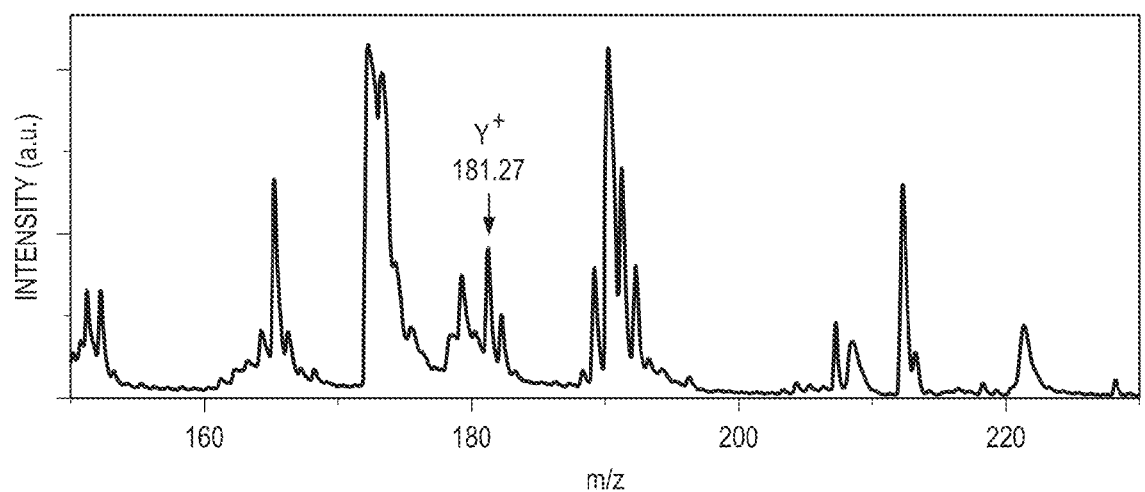
Figure 8D:
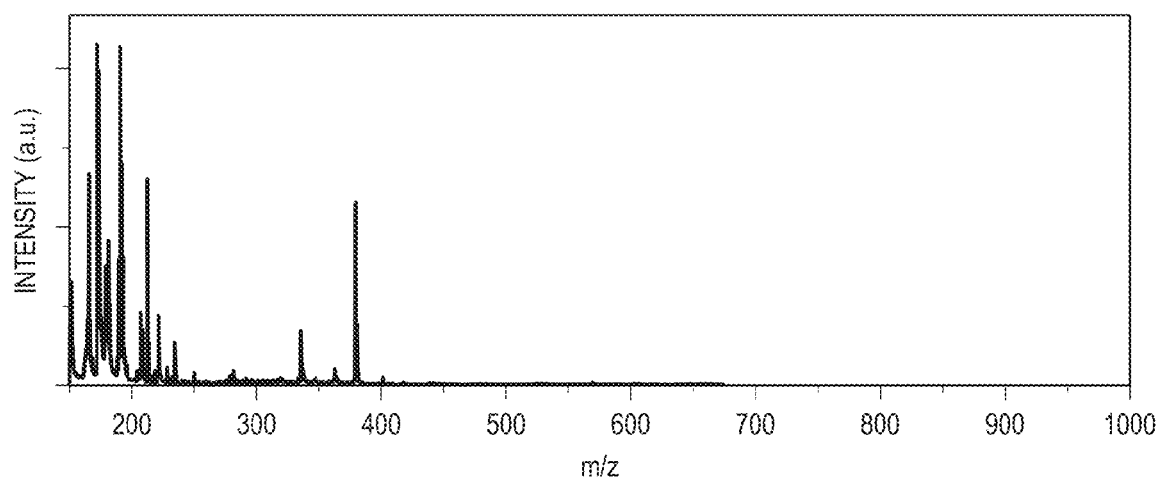
Figure 9A:
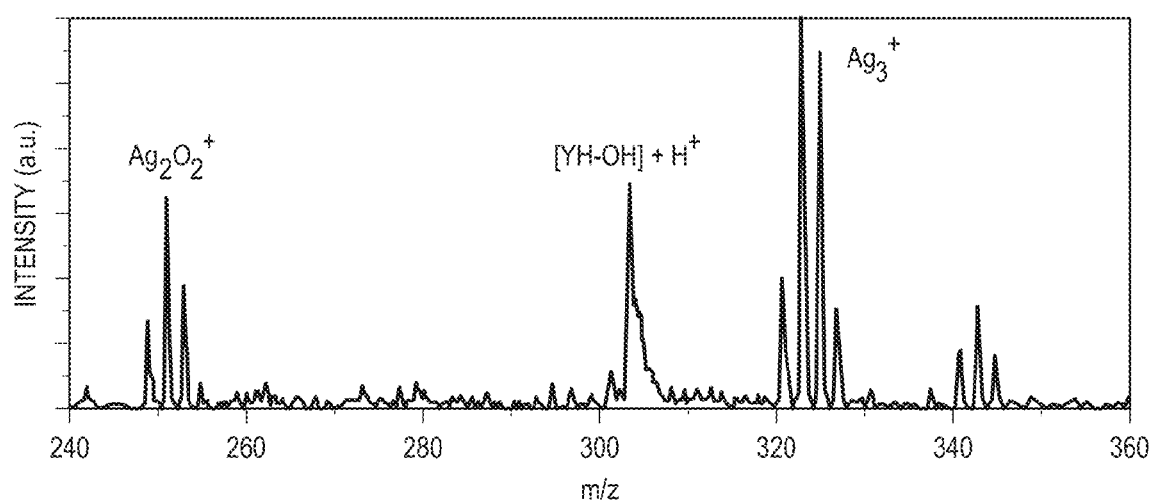
FIGS. 9A-9D show: the magnified MALDI-TOF spectra of YH peptide with Ag nanoparticles (FIG. 9A), original MALDI-TOF spectra of YH with Ag nanoparticles showing no low mass interference with peptide (FIG. 9B), magnified MALDI-TOF spectra of YH in CHCA matrix (FIG. 9C), and original MALDI-TOF spectra of YH in CHCA matrix showing low mass interference with peptide (FIG. 9D)
Figure 9B:
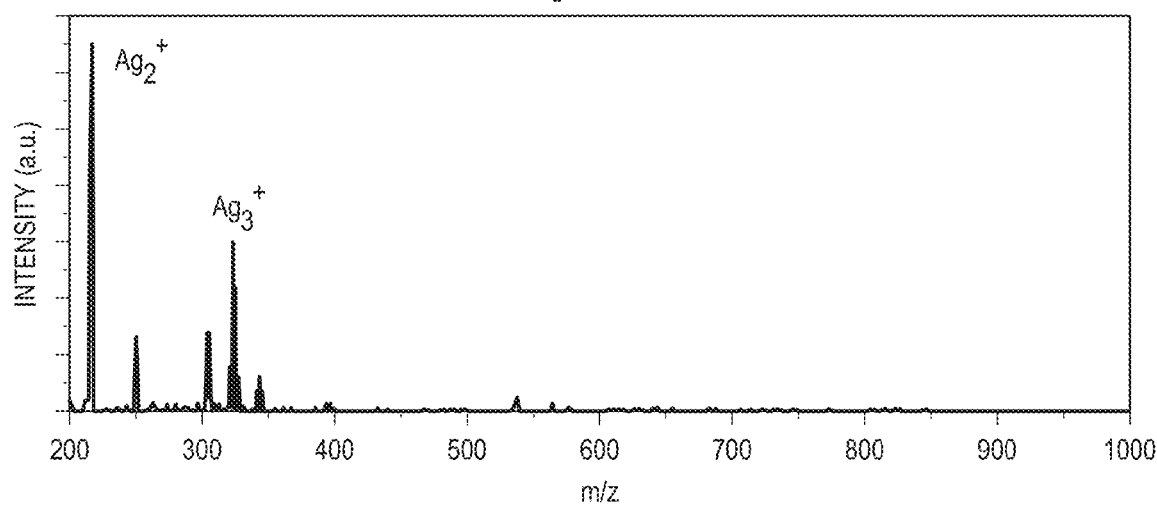
Figure 9C:
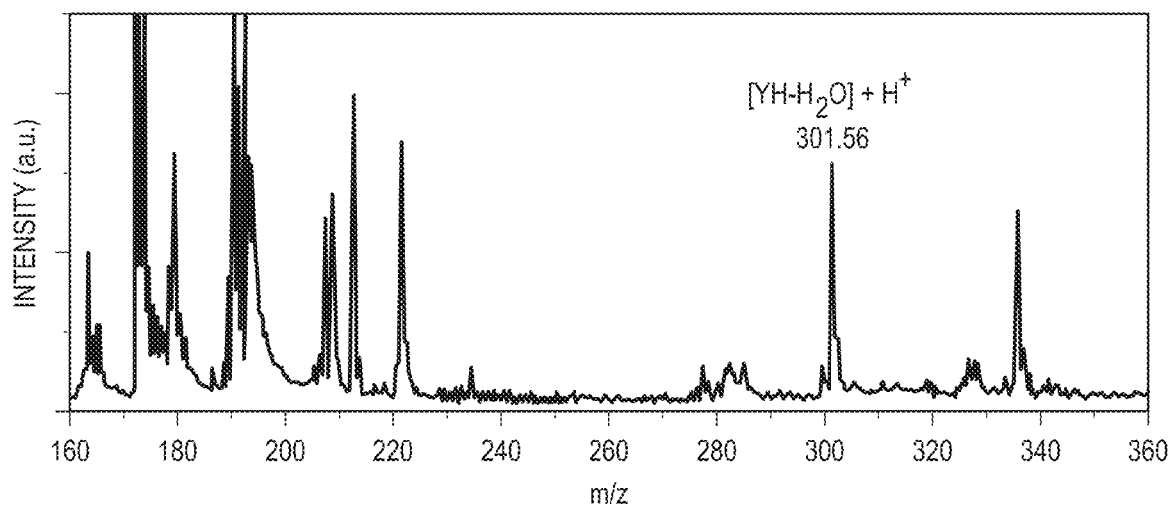
Figure 9D:
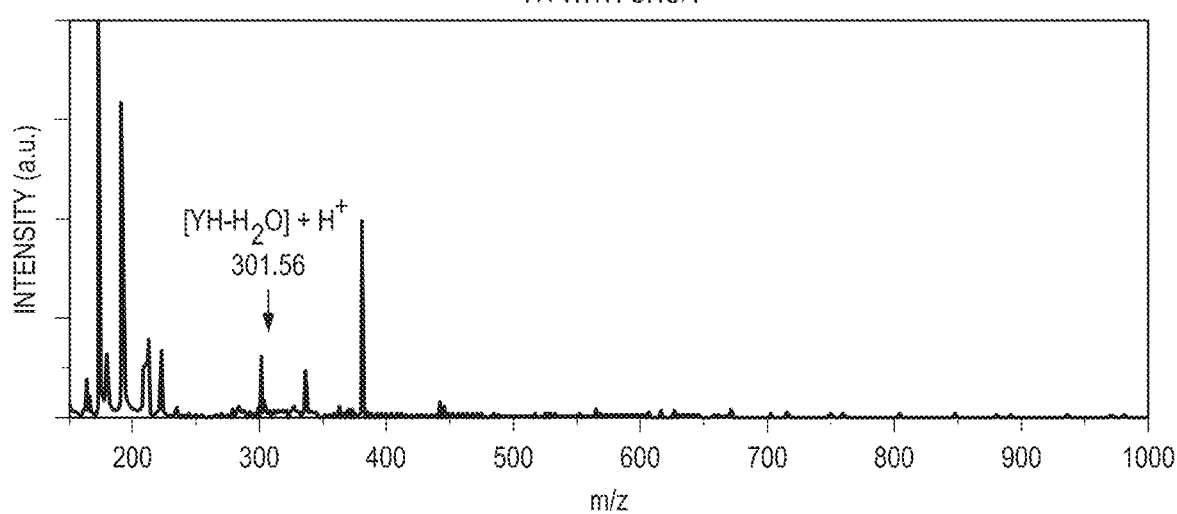
Figure 10A:
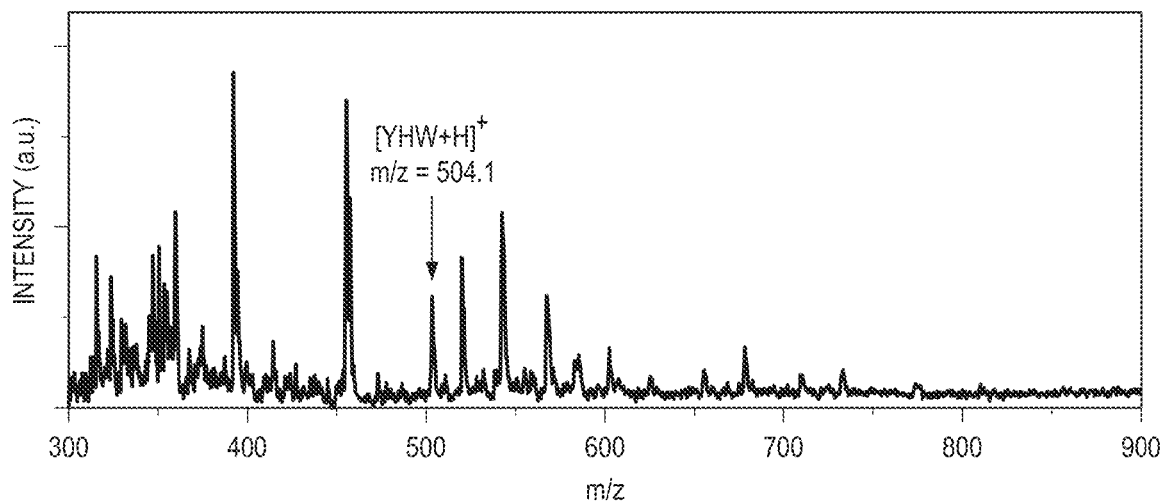
FIGS. 10A and 10B show: MALDI-TOF spectra using CHCA matrix with YHW (FIG. 10A) and MALDI-TOF spectra of YHW using Ag nanoparticles (FIG. 10B).
Figure 10B:
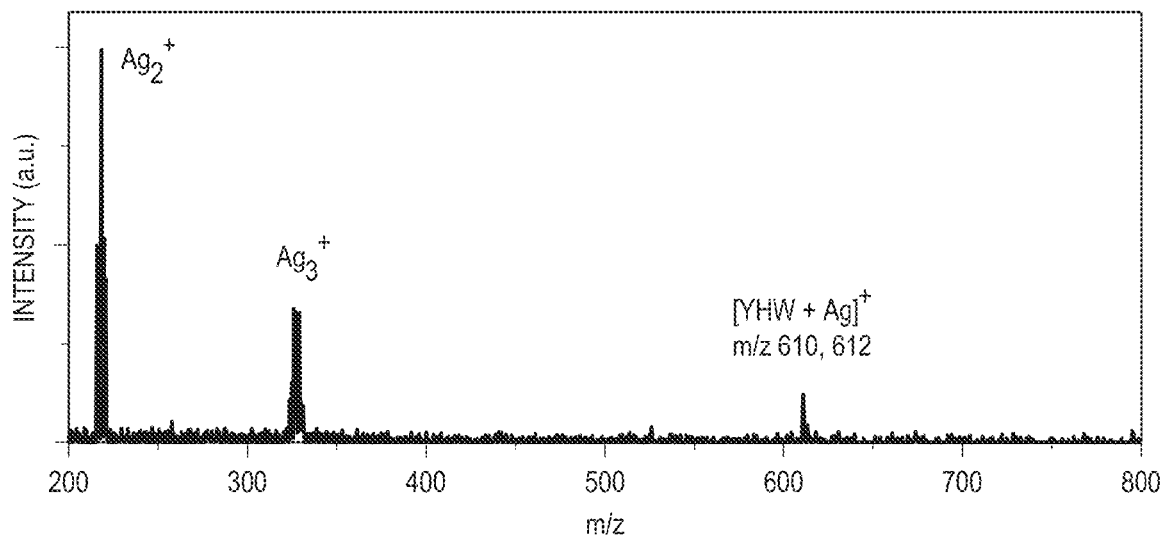

Comparisons of peptide spectra based on soft landed Ag nanoparticles vs. standard matrices (CHCA) show significant decrease in matrix/analyte interference as well as an overall increase in the S/N ratio for the soft landed nanoparticles. A problem that has plagued MALDI over the years is the amount of time it takes to prepare a sample. Certain samples like oligonucleotides, may require the addition of fucose or spearmine to the matrix in order to improve the MALDI process and clean up the spectra [45, 46]. Carbohydrates, sugars, and other chemicals have also been added to matrices for this same purpose [46-50]. Salts, buffers or chemical additives may be needed to adjust the pH to help the matrix crystallize uniformly with preparation lasting anywhere from 30 minutes to 2 hours depending on the analyte and whether solution preparation required for analysis. Where with soft landing we can spot a MALDI with a simple analyte solution of 1:1 (V:V) MeOH/H$_2$O with 0.1% TFA and allowed to dry. Once the analyte has dried, Ag nanoparticles are deposited for 15 minutes finalizing all sample preparations in less than 40 minutes. Through the use of soft landing we are able to reduce matrix/analyte interference and increase the S/N of the spectrum. Another limitation of traditional MALDI matrices is the inability to complete analysis in the low mass regime (between 200-800 da) with standard matrices. However SLIM-MALDI increases the viability of low mass analysis [48]. FIGS. 8-10 clearly show the difference in spectra between Ag soft landed nanoparticles and CHCA. The two recognizable peaks in the soft landed nanoparticle spectra have almost no interference in the low mass range except with compounds in the m/z range of Ag$_n^+$ clusters peaks of n=2-3. The other masses present in the spectra FIGS. 8A, 8B, 9A, 9B, and 10B are that of the amino acid [Y—H$_2$O]+H$^+$ (m/z=163), [Y+H]$^+$ (FIG. 8A), [YH—H$_2$O]+H$^+$ (FIGS. 9A and 9B), and [YHW+Ag]$^+$ (FIG. 10B). In FIG. 8A, [Y+H]$^+$ was assigned to m/z 181 due to the increased S/N even though the signal is clearly not within 3σ of the baseline. The signal is identifiable and present within the Ag nanoparticle matrix spectra. The same could not be said of the CHCA spectra which shows significant interference from matrix causing the [Y+H]$^+$ (m/z 181) and [YHW+H]$^+$ peptide peak (m/z 504) to be indistinguishable from the remaining masses. TOF data shows that SLIM-MALDI is viable as a technique and source for the creation of low mass MALDI matrices.

The technique of using SLIM of Ag nanoparticles as a MALDI matrix as described herein is a novel. The data presented herein highlights the benefits of this technique which are a quick and simple sample preparation (ready in less than 40 minutes), the capability to look at the low mass range on TOF without matrix interference, and the benefit of increased S/N ratio. The soft landing of Ag clusters as a MALDI matrix is viable even though the adducting of Ag$^+$ to the peptide compounds is not preferred, and neither is the reduced ionization efficiency. Through continued development, characterization, and manipulation of nanoparticle sizes through KE control the inventors were able to determine the optimum particle size and composition. The inventors can fully utilize SLIM as a MALDI preparation source not just for low mass compounds but high mass compounds as well aiding in imaging tissue and making the low mass markers available for determination.

The utility of silver nanoparticles as a sample matrix along with a novel method for nanoparticle development has been described hereinabove. Silver nanoparticles were generated from silver ions on the surface of a MALDI plate utilizing a Soft Landing Ion Mobility (SLIM) instrument developed by the present inventors. Upon interaction with the surface the incident silver ions were labile and aggregated into the nanoparticle structures in a time dependent fashion. Post landing TOF-MS analysis, showed elimination of low mass interference peaks in the spectra. The lack of low mass interferences allowed detection of low mass analytes along with the silver adduct peak in some cases. Also noted in these spectra were the lack of fragmentation and an increased signal to noise ratio, indicating that silver being deposited was acting as a suitable matrix. The SLIM-MALDI based approach of the present invention significantly decreased sample preparation time and may lead to a preparation free MALDI source by soft landing a matrix directly on the sample surface.

It is contemplated that any embodiment discussed in this specification can be implemented with respect to any method, kit, reagent or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C or combinations thereof" is intended to include at least one of: A, B, C, AB, AC, BC or ABC, and if order is important in a particular context, also BA, CA, CB, CBA, BCA, ACB, BAC or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 7,202,472: Mass Spectrometric Analysis Using Nanoparticles.
U.S. Patent Application No. 2010/0090105: Ionization Device.
U.S. Pat. No. 7,122,792: Metal Oxide-Assisted Laser Desorption/Ionization Mass Spectrometry.
1. Karas, M.; Bachmann, D.; Hillenkamp, F., Influence of the wavelength in high-irradiance ultraviolet laser desorption mass spectrometry of organic molecules, Anal. Chem. 1985, 57 (14), 2935-2939.
2. Beavis, R. C.; Chait, B. T.; Fales, H. M., Cinnamic acid derivatives as matrices for ultraviolet laser desorption mass spectrometry of proteins, Rapid Commun. Mass Spectrom. 1989, 3 (12), 432-435.
3. Strupat, K.; Karas, M.; Hillenkamp, F., 2,5-Dihydroxybenzoic acid: a new matrix for laser desorption—ionization mass spectrometry, Int. J. Mass Spectrom. Ion Processes 1991, 111, 89-102.
4. Fitzgerald, M. C.; Parr, G. R.; Smith, L. M., Basic matrixes for the matrix-assisted laser desorption/ionization mass spectrometry of proteins and oligonucleotides, Anal. Chem. 1993, 65 (22), 3204-3211.
5. Beavis, R. C.; Chait, B. T.; Standing, K. G., Matrix-assisted laser-desorption mass spectrometry using 355 nm radiation, Rapid Commun. Mass Spectrom. 1989, 3 (12), 436-439.
6. Beavis, R. C.; Chaudhary, T.; Chait, B. T., alpha-Cyano-4-hydroxycinnamic acid as a matrix for matrix assisted laser desorption mass spectrometry, Org. Mass Spectrom. 1992, 27 (2), 156-158.
7. Zenobi, R.; Knochenmuss, R., Ion formation in MALDI mass spectrometry, Mass Spectrom. Rev. 1998, 17 (5), 337-366.
8. Knochenmuss, R., Ion formation mechanisms in UV-MALDI, The Analyst 2006, 131 (9), 966-986.
9. Gusev, A. I.; Wilkinson, W. R.; Proctor, A.; Hercules, D. M., Improvement of signal reproducibility and matrix/co-matrix effects in MALDI analysis, Anal. Chem. 1995, 67 (6), 1034-1041.
10. McLean, J. A.; Stumpo, K. A.; Russell, D. H., Size-Selected (2-10 nm) Gold Nanoparticles for Matrix Assisted Laser Desorption Ionization of Peptides, J. Am. Chem. Soc. 2005, 127 (15), 5304-5305.
11. Guan, B.; Lu, W.; Fang, J.; Cole, R. B., Characterization of Synthesized Titanium Oxide Nanoclusters by MALDI-TOF Mass Spectrometry, J. Am. Soc. Mass. Spectrom. 2007, 18 (3), 517-524.
12. Chensong, P.; Songyun, X.; Ligang, H.; Xingye, S.; Junjie, O.; Hanfa, Z.; Zhong, G.; Yu, Z.; Baochuan, G., Using oxidized carbon nanotubes as matrix for analysis of small molecules by MALDI-TOF MS, J Am Soc Mass Spectrom 2005, 16 (6), 883-92.
13. Go, E. P.; Prenni, J. E.; Wei, J.; Jones, A.; Hall, S. C.; Witkowska, H. E.; Shen, Z.; Siuzdak, G., Desorption/Ionization on. Silicon Time-of-Flight/Time-of-Flight Mass Spectrometry, Anal. Chem. 2003, 75 (10), 2504-2506.
14. Tanaka, K.; Waki, H.; Ido, Y.; Akita, S.; Yoshida, Y.; Yoshida, T.; Matsuo, T., Protein and polymer analyses up to <I>m/z</I>100 000 by laser ionization time-of-flight mass spectrometry, Rapid Commun. Mass Spectrom. 1988, 2 (8), 151-153.
15. Dong, X.; Cheng, J.; Li, J.; Wang, Y., Graphene as a Novel Matrix for the Analysis of Small Molecules by MALDI-TOF MS, Anal. Chem. 2010, 82 (14), 6208-6214.
16. Sherrod, S. D.; Diaz, A. J.; Russell, W. K.; Cremer, P. S.; Russell, D. H., Silver Nanoparticles as Selective Ionization Probes for Analysis of Olefins by Mass Spectrometry, Anal. Chem. 2008, 80 (17), 6796-6799.
17. Gholipour, Y.; Giudicessi, S. L.; Nonami, H.; Erra-Balsells, R., Diamond, Titanium Dioxide, Titanium Silicon Oxide, and Barium Strontium Titanium Oxide Nanoparticles as Matrixes for Direct Matrix-Assisted Laser Desorption/Ionization Mass Spectrometry Analysis of Carbohydrates in Plant Tissues, Anal. Chem. 2010, 82 (13), 5518-5526.
18. Xu, S.; Li, Y.; Zou, H.; Qiu, J.; Guo, Z.; Guo, B., Carbon Nanotubes as Assisted Matrix for Laser Desorption/Ionization Time-of-Flight Mass Spectrometry, Anal. Chem. 2003, 75 (22), 6191-6195.
19. Cuiffi, J. D.; Hayes, D. J.; Fonash, S. J.; Brown, K. N.; Jones, A. D., Desorption-Ionization Mass Spectrometry Using Deposited Nanostructured Silicon Films, Anal. Chem. 2001, 73 (6), 1292-1295.
20. Shariatgorji, M.; Amini, N.; Ilag, L., Silicon nitride nanoparticles for surface-assisted laser desorption/ionization of small molecules, J. Nanopart. Res. 2009, 11 (6), 1509-1512.
21. Sunner, J.; Dratz, E.; Chen, Y.-C., Graphite surface-assisted laser desorption/ionization time-of-flight mass spectrometry of peptides and proteins from liquid solutions, Anal. Chem. 1995, 67 (23), 4335-4342.
22. Wu, H.-P.; Yu, C.-J.; Lin, C.-Y.; Lin, Y.-H.; Tseng, W.-L., Gold Nanoparticles as Assisted Matrices for the Detection of Biomolecules in a High-Salt Solution through Laser Desorption/Ionization Mass Spectrometry, J. Am. Soc. Mass. Spectrom. 2009, 20 (5), 875-882.
23. Hua, L.; Chen, J.; Ge, L.; Tan, S., Silver nanoparticles as matrix for laser desorption/ionization mass spectrometry of peptides, J. Nanopart. Res. 2007, 9 (6), 1133-1138.
24. Su, C.-L.; Tseng, W.-L., Gold Nanoparticles as Assisted Matrix for Determining Neutral Small Carbohydrates through Laser Desorption/Ionization Time-of-Flight Mass Spectrometry, Anal. Chem. 2007, 79 (4), 1626-1633.
25. Ernest K. Lewis, T. F. E., Sasa Miladinovic, Shelley N. Jackson, Amina S. Woods, Charles L. Wilkins, J. Albert Schultz, Giant Fullerenes as in-situ internal calibrants for high mass accuracy MALDI-IM-oTOF-MS for tissues imaging. In ASMS 58th annual Conference Ionwerks, Ed. Salt Lake City, Utah, 2010.
26. Davila, S. J.; Birdwell, D. O.; Verbeck, G. F., Drift tube soft-landing for the production and characterization of materials: Applied to Cu clusters, Rev. Sci. Instrum. 2010, 81 (3), 034104-6.
27. Franchetti, V.; Solka, B. H.; Baitinger, W. E.; Amy, J. W.; Cooks, R. G., Soft landing of ions as a means of surface modification, International Journal or Mass Spectrometry and Ion Physics 1977, 23 (1), 29-35.28.
28. Volný, M.; Elam, W. T.; Branca, A.; Ratner, B. D.; Tureček, F., Preparative Soft and Reactive Landing of Multiply Charged Protein Ions on a Plasma-Treated Metal Surface, Anal. Chem. 2005, 77 (15), 4890-4896.
29. Alvarez, J.; Cooks, R. G.; Barlow, S. E.; Gaspar, D. J.; Futrell, J. H.; Laskin, J., Preparation and in Situ Characterization of Surfaces Using Soft Landing in a Fourier Transform Ion Cyclotron Resonance Mass Spectrometer, Anal. Chem. 2005, 77 (11), 3452-3460.
30. Tong, X.; Benz, L.; Kemper, P.; Metiu, H.; Bowers, M. T.; Buratto, S. K., Intact Size-Selected Aun Clusters on a TiO2 (110)-(1×1) Surface at Room Temperature, J. Am. Chem. Soc. 2005, 127 (39), 13516-13518.
31. Peng, W.-P.; Goodwin, M. P.; Nie, Z.; Volný, M.; Ouyang, Z.; Cooks, R. G., Ion Soft Landing Using a Rectilinear Ion Trap Mass Spectrometer, Anal. Chem. 2008, 80 (17), 6640-6649.
32. Albritton, D. L.; Miller, T. M.; Martin, D. W.; McDaniel, E. W., Mobilities of Mass-Identified $H_2^{+}$ and $H^{+}$ Ions in Hydrogen, Physical Review 1968, 171 (1), 94.
33. Eiber, H., Behavior of negative and positive Ions in pure oxygen and in oxygen-water vapor mixtures, Zeitschrift fuer Angewandte 1963, 15, 103-112.
34. Hill, H. H.; Siems, W. F.; St. Louis, R. H., Ion mobility spectrometry, Anal. Chem. 1990, 62 (23), 1201A-1209A.
35. Wannier, G. H., Motion of Gaseous Ions in Strong Electric Fields, The Bell System Technical Journal 1953, 32 (1), 170-254.
36. Eiceman, G. A. K., Z., Ion Mobility Spectrometry, Second Edition CRC Press: Boca Raton, Fla., 2005; p 370.
37. Mason, E. A., McDaniel, E. W., Transport Properties of Ions in Gases. Wiley-Interscience Publication New York, N.Y., 1988.
38. Bhattacharyya, K. G., Adsorption of carbon dioxide on mica surfaces, Langmuir 1989, 5 (5), 1155-1162.
39. Brown, J. M.; Hoffmann, W. D.; Alvey, C. M.; Wood, A. R.; Verbeck, G. F.; Petros, R. A., One-bead, one-compound peptide library sequencing via high-pressure ammonia cleavage coupled to nanomanipulation/nanoelectrospray ionization mass spectrometry, Anal. Biochem. 2010, 398 (1), 7-14.
40. Taylor, W. S.; Spicer, E. M.; Barnas, D. F., Metastable Metal Ion Production in Sputtering dc Glow Discharge Plasmas: Characterization by Electronic State Chromatography, The Journal of Physical Chemistry A 1999, 103 (5), 643-650.
41. Kemper, P. R.; Bowers, M. T., Electronic-state chromatography: application to first-row transition-metal ions, The Journal of Physical Chemistry 1991, 95 (13), 5134-5146.
42. Bowers, M. T.; Kemper, P. R.; Gert von, H.; Koppen, P. A. M. v., Gas-Phase Ion Chromatography: Transition Metal State Selection and Carbon Cluster Formation, Science 1993, 260 (5113), 1446-1451.

43. Bray, K. R.; Parsons, G. N., Surface transport kinetics in low-temperature silicon deposition determined from topography evolution, Physical Review B 2001, 65 (3), 035311.
44. Oviedo, O. A.; et al., Diffusion mechanisms taking place at the early stages of cobalt deposition on Au(111), J. Phys.: Condens. Matter 2008, 20 (26), 265010.
45. Asara, J. M.; Allison, J., Enhanced Detection of Oligonucleotides in UV MALDI MS Using the Tetraamine Spermine as a Matrix Additive, Anal. Chem. 1999, 71 (14), 2866-2870.
46. Distler, A. M.; Allison, J., Improved MALDI-MS Analysis of Oligonucleotides through the Use of Fucose as a Matrix Additive, Anal. Chem. 2001, 73 (20), 5000-5003.
47. Kjellström, S.; Jensen, O. N., Phosphoric Acid as a Matrix Additive for MALDI MS Analysis of Phosphopeptides and Phosphoproteins, Anal. Chem. 2004, 76 (17), 5109-5117.
48. Cohen, L.; Gusev, A., Small molecule analysis by MALDI mass spectrometry, Analytical and Bioanalytical Chemistry 2002, 373 (7), 571-586.
49. Billeci, T. M.; Stults, J. T., Tryptic mapping of recombinant proteins by matrix-assisted laser desorption/ionization mass spectrometry, Anal. Chem. 1993, 65 (13), 1709-1716.
50. Cohen, S. L.; Chait, B. T., Influence of Matrix Solution Conditions on the MALDI-MS Analysis of Peptides and Proteins, Anal. Chem. 1996, 68 (1), 31-37.

What is claimed is:

1. A method for identifying, detecting, analyzing or combinations thereof one or more low mass analytes by a matrix-assisted laser desorption/ionization-time of flight mass spectrometry (MALDI-TOF MS) technique comprising the steps of:
providing a liquid sample comprising the one or more low mass analytes to be identified, detected or analyzed;
depositing the liquid sample on a surface of a MALDI plate or a substrate, wherein the liquid sample is dried on the surface of the MALDI plate or the substrate;
depositing a matrix comprising one or more metal nanoparticles, clusters or combinations thereof on the surface of the MALDI plate or substrate comprising the dried liquid sample, wherein the metal nanoparticles or clusters are deposited or soft landed on the surface of the MALDI plate or substrate by a gas phase mobility soft landing method, wherein the soft landing method comprises a SLIM, a differential mobility analyzer (DMA), a drift tube (DT) or a flow tube (FT) comprising the steps of:
providing an instrument comprising a drift region or a drift tube and a split-ring ion optic deflector, wherein the ion optic deflector helps selects and soft land a cluster of metal ions of a specific mobility;
ionizing a target, a sample, a composition or a combinations thereof comprising at least one component capable of generating one or more metal ions by laser ablation in the instrument;
separating and thermalizing the one or more metal ions in the drift region of the instrument by collision with a high pressure inert bath gas or gas mixture contained in the instrument;
directing the thermalized metal ions using the split-ring ion optic from the drift tube to a landing surface, wherein the landing surface comprises the MALDI plate or the substrate;
soft-landing the one or more metal ions on the MALDI plate or the substrate; and
continuing the soft-landing for a specified period of time until a desired metal nanoparticle or cluster size is obtained;
placing the MALDI plate or the substrate comprising the dried sample and the metal nanoparticle matrix in MALDI-TOF mass spectrometer;
obtaining a MALDI-TOF spectra by operating the MALDI-TOF mass spectrometer; and
identifying, detecting or analyzing the one or more low mass analytes by a m/z ratio in the MALDI-TOF spectra.

2. The method of claim 1, wherein the low mass analytes comprise peptides, amino acids, small proteins, small molecules, organic compounds, organometallic compounds, inorganic compounds, and combinations or modifications thereof.

3. The method of claim 1, wherein the one or more metal nanoparticles comprise silver, titanium, gold, platinum, palladium, nickel, cobalt, copper or manganese nanoparticles.

4. The method of claim 1, wherein the nanoparticle is a silver nanoparticle.

5. The method of claim 1, wherein the one or more metal nanoparticles have an average size of about 10-500 nm.

6. The method of claim 1, wherein the one or more metal nanoparticles have an average size of 10 nm, 25 nm, 50 nm, 75 nm, 100 nm, 150 nm, 200 nm, 225 nm, 250 nm, 275 nm, 300 nm, 350 nm, 400 nm, 450 nm, and 500 nm.

7. The method of claim 1, wherein the metal nanoparticles eliminate or minimize one or more low mass interference peaks from the MALDI-TOF spectra.

8. The method of claim 1, wherein the metal nanoparticles increase a signal to noise (S/N) ratio in the MALDI-TOF spectra.

9. The method of claim 1, wherein the MALDI-TOF spectra may comprise one or more peaks relating to adduct products from the metal nanoparticles in the matrix.

10. A system for identifying, detecting or analyzing one or more low mass analytes in a sample comprising:
a matrix-assisted laser desorption/ionization-time of flight mass spectrometer (MALDI-TOF MS); and
a MALDI plate or a substrate comprising the sample and a matrix of one or more metal nanoparticles or clusters, wherein the MALDI plate or the substrate is placed in the MALDI-TOF MS, wherein the metal nanoparticles or clusters are deposited or soft landed on the MALDI plate or a substrate by a gas phase mobility soft landing instrument comprising:
a soft landing chamber (SL) in a housing;
a laser source capable of generating a laser pulse or a radiation for an ionization of a target, a sample, a composition or a combination thereof comprising at least one component capable of generating one or more metal ions by laser ablation;
a drift region or a drift tube for separating and thermalizing the one or more metal ions by collisions with a high pressure inert bath gas or gas mixture contained in the drift tube, wherein an electric potential can be applied to the drift tube, wherein the drift tube further comprises two split rings placed at the two ends of the drift tube, for directing an ion cluster beam emanating from the drift tube, wherein a pulsed voltage can be applied to the split rings;
a high voltage power supply for powering the drift tube, generating an electric field for the migration of the one or more metal ions;
a pulsing circuit for providing either a positive or a negative pulsed voltage;

a flange or similar arrangement to remove or replace the landing surface, wherein the landing surface comprises the MALDI plate or the substrate; and a rotary vane rough pump for allowing the instrument to attain a low pressure.

11. The system of claim 10, wherein the low mass analytes comprise peptides, amino acids, small proteins, small molecules, organic compounds, organometallic compounds, inorganic compounds, and combinations or modifications thereof.

12. The system of claim 10, wherein the one or more metal nanoparticles comprise silver, titanium, gold, platinum, palladium, nickel, cobalt, copper or manganese nanoparticles.

13. The system of claim 10, wherein the nanoparticle is a silver nanoparticle.

14. The system of claim 10, wherein the one or more metal nanoparticles have an average size of about 10-500 nm.

15. The system of claim 10, wherein the metal nanoparticles eliminate or minimize one or more low mass interference peaks from a MALDI-TOF spectra, increase a signal to noise (S/N) ratio in the MALDI-TOF spectra or both.

16. The system of claim 15, wherein the MALDI-TOF spectra may comprise one or more peaks relating to adduct products from the metal nanoparticles in the matrix.

17. A method for depositing a matrix comprising one or more metal nanoparticles on a surface of a matrix-assisted laser desorption (MALDI) plate by a gas phase mobility soft landing method comprising the steps of:

providing an instrument comprising a drift region or drift tube and a split-ring ion optic deflector, wherein the ion optic deflector helps selects and soft land a cluster of metal ions of a specific mobility;

ionizing a target, a sample, a composition or a combinations thereof comprising at least one component capable of generating one or more metal ions by laser ablation in the instrument;

separating and thermalizing the one or more metal ions in the drift tube of the instrument by collision with a high pressure inert bath gas or gas mixture contained in the drift tube;

directing the thermalized metal ions using the split-ring ion optic from the drift tube to a landing surface, wherein the landing surface comprises the MALDI plate or the substrate;

soft-landing the one or more metal ions on the MALDI plate or the substrate; and continuing the soft-landing for a specified period of time until a desired metal nanoparticle is obtained.

18. The method of claim 17, wherein the matrix is used to identify, detect or analyze one of more low mass analytes in a sample by a matrix-assisted laser desorption/ionization-time of flight mass spectrometry (MALDI-TOF MS) technique, wherein the sample is deposited on the surface of the MALDI plate prior to depositing the one or more nanoparticles, wherein the low mass analytes comprise peptides, amino acids, small proteins, small molecules, organic compounds, organometallic compounds, inorganic compounds, and combinations or modifications thereof.

19. The method of claim 17, wherein the one or more metal nanoparticles comprise silver, titanium, gold, platinum, palladium, nickel, cobalt, copper or manganese nanoparticles.

20. The method of claim 17, wherein the nanoparticle is a silver nanoparticle.

21. The method of claim 17, wherein the one or more metal nanoparticles have an average size of about 10-500 nm.

22. The method of claim 17, wherein the one or more metal nanoparticles have an average size of 10 nm, 50 nm, 100 nm, 150 nm, 200 nm, 225 nm, 250 nm, 275 nm, 300 nm, 350 nm, 400 nm, 450 nm, and 500 nm.

23. An instrument for depositing a matrix comprising one or more metal nanoparticles on a surface of a matrix-assisted laser desorption (MALDI) plate by a gas phase mobility soft landing method comprising:

a soft landing chamber (SL) in a housing;

a laser source capable of generating a laser pulse or a radiation for an ionization of a target, a sample, a composition or a combination thereof comprising at least one component capable of generating the one or more metal ions to be deposited by laser ablation;

a drift region or drift tube for separating and thermalizing the one or more metal ions by collisions with a high pressure inert bath gas or gas mixture contained in the drift tube, wherein an electric potential can be applied to the drift tube, wherein the drift tube further comprises two split rings placed at the two ends of the drift tube, for directing an ion cluster beam emanating from the drift tube, wherein a pulsed voltage can be applied to the split rings;

a high voltage power supply for powering the drift tube, generating an electric field for the migration of the one or more metal ions;

a pulsing circuit for providing either a lower positive or a lower negative pulsed voltage;

a flange or similar arrangement to remove or replace the landing surface, wherein the landing surface comprises the MALDI plate; and a rotary vane rough pump for allowing the instrument to attain a low pressure.

24. The instrument of claim 23, wherein the matrix is used to identify, detect or analyze one of more low mass analytes in a sample by a matrix-assisted laser desorption/ionization-time of flight mass spectrometry (MALDI-TOF MS) technique, wherein the sample is deposited on the surface of the MALDI plate prior to depositing the one or more nanoparticles, wherein the low mass analytes comprise peptides, amino acids, small proteins, small molecules, organic compounds organometallic compounds, inorganic compounds, and combinations or modifications thereof.

25. The instrument of claim 23, wherein the one or more metal nanoparticles comprise silver, titanium, gold, platinum, palladium, nickel, cobalt, copper or manganese nanoparticles.

26. The instrument of claim 23, wherein the nanoparticle is a silver nanoparticle.

27. The instrument of claim 23, wherein the one or more metal nanoparticles have an average size of about 10-500 nm.

28. A method for identifying, detecting, analyzing or combinations thereof one or more peptides by a matrix-assisted laser desorption/ionization-time of flight mass spectrometry (MALDI-TOF MS) technique comprising the steps of:

providing a liquid sample comprising the one or more peptides to be identified, detected or analyzed;

depositing the liquid sample on a surface of a MALDI plate, wherein the liquid sample is dried on the surface of the MALDI plate;

depositing a matrix comprising one or more silver nanoparticles on the surface of the MALDI plate comprising the dried liquid sample, wherein the silver nanoparticles are soft landed on the surface of the MALDI plate by a gas phase mobility soft landing method comprising the steps of:

providing an instrument comprising a drift region or drift tube and a split-ring ion optic deflector, wherein the ion optic deflector helps selects and soft land a cluster of silver ions of a specific mobility;

ionizing a silver rod capable of generating one or more silver ions by laser ablation in the instrument;

separating and thermalizing the one or more silver ions in the drift tube of the instrument by collision with helium gas or gas mixture contained in the drift tube;

directing the thermalized metal ions using the split-ring ion optic from the drift tube to the MALDI plate;

soft-landing the one or more silver ions on the MALDI plate; and continuing the soft-landing for a specified period of time until a desired silver nanoparticle size is obtained;

placing the MALDI plate comprising the dried sample and the silver nanoparticle matrix in MALDI-TOF mass spectrometer;

obtaining a MALDI-TOF spectra by operating the MALDI-TOF mass spectrometer; and identifying, detecting or analyzing the one or more peptides by a m/z ratio in the MALDI-TOF spectra.

29. The method of claim 28, wherein the peptides comprise tyrosine-histidine (YH) or tyrosine-histidine-tryptophan (YHW).

30. The method of claim 28, wherein the one or more silver nanoparticles have an average size of about 10-500 nm.

31. The method of claim 28, wherein the one or more silver nanoparticles have an average size of 10 nm, 25 nm, 50 nm, 75 nm, 100 nm, 150 nm, 200 nm, 225 nm, 250 nm, 275 nm, 300 nm, 350 nm, 400 nm, 450 nm, and 500 nm.

32. The method of claim 28, wherein the silver nanoparticles eliminate or minimize one or more low mass interference peaks from the MALDI-TOF spectra.

33. The method of claim 28, wherein the silver nanoparticles increase a signal to noise (S/N) ratio in the MALDI-TOF spectra.

34. The method of claim 28, wherein the MALDI-TOF spectra may comprise one or more peaks relating to adduct products from the silver nanoparticles in the matrix.

35. A system for identifying, detecting or analyzing one or more peptides in a sample comprising:

a matrix-assisted laser desorption/ionization-time of flight mass spectrometer (MALDI-TOF MS); and a MALDI plate comprising the sample and a matrix of one or more silver nanoparticles, wherein the MALDI plate or a substrate is placed in the MALDI-TOF MS, wherein the silver nanoparticles are deposited or soft landed on the MALDI plate by a gas phase mobility soft landing instrument comprising:

a soft landing chamber (SL) in a housing;

a laser source capable of generating a laser pulse or a radiation for an ionization of a silver rod for generating one or silver metal ions by laser ablation;

a drift region or drift tube for separating and thermalizing the one or more silver ions by collisions with a high pressure helium gas or gas mixture contained in the drift tube, wherein an electric potential can be applied to the drift region or the drift tube, wherein the drift region or the drift tube further comprises two split rings placed at the two ends of the drift tube for directing an ion cluster beam emanating from the drift tube, wherein a pulsed voltage can be applied to the split rings;

a high voltage power supply for powering the drift tube, generating an electric field for the migration of the one or more silver ions;

a pulsing circuit for providing either a positive or a negative pulsed voltage;

a flange or similar arrangement to remove or replace the MALDI plate; and a rotary vane rough pump for allowing the instrument to attain a low pressure.

36. The system of claim 35, wherein the one or more silver nanoparticles have an average size of about 10-500 nm.

37. The system of claim 35, wherein the silver nanoparticles eliminate or minimize one or more low mass interference peaks from the MALDI-TOF spectra.

38. The system of claim 35, wherein the silver nanoparticles increase a signal to noise (S/N) ratio in the MALDI-TOF spectra.

39. The system of claim 35, wherein the MALDI-TOF spectra may comprise one or more peaks relating to adduct products, clusters or both relating to the silver nanoparticles in the matrix.

* * * * *